(12) United States Patent
Hasse et al.

(10) Patent No.: US 8,252,863 B2
(45) Date of Patent: Aug. 28, 2012

(54) RUBBER MIXTURES

(75) Inventors: Andre Hasse, Linnich-Ederen (DE);
Karsten Korth, Grenzach-Wyhlen (DE);
Ingo Kiefer, Schwörstadt-Dossenbach (DE); Susann Witzsche, Rheinfelden (DE); Philipp Albert, Lörrach (DE);
Oliver Klockmann, Niederzier (DE)

(73) Assignee: Evonik Degussa GmbH, Essen (DE)

( * ) Notice: Subject to any disclaimer, the term of this patent is extended or adjusted under 35 U.S.C. 154(b) by 421 days.

(21) Appl. No.: 12/159,942

(22) PCT Filed: Jan. 9, 2007

(86) PCT No.: PCT/EP2007/050174
§ 371 (c)(1),
(2), (4) Date: May 7, 2009

(87) PCT Pub. No.: WO2007/085521
PCT Pub. Date: Aug. 2, 2007

(65) Prior Publication Data
US 2009/0221751 A1    Sep. 3, 2009

(30) Foreign Application Priority Data
Jan. 28, 2006    (DE) .................. 10 2006 004 062

(51) Int. Cl.
*C08L 83/00* (2006.01)
(52) U.S. Cl. ......... 524/506; 524/262; 524/386; 556/408
(58) Field of Classification Search .................. 556/408; 524/262, 386, 506
See application file for complete search history.

(56) References Cited

U.S. PATENT DOCUMENTS

| | | | |
|---|---|---|---|
| 3,978,103 A | | 8/1976 | Meyer-Simon et al. |
| 3,997,581 A | * | 12/1976 | Pletka et al. .................. 556/408 |
| 4,048,206 A | * | 9/1977 | Voronkov et al. ............. 556/405 |
| 6,433,206 B1 | | 8/2002 | Gedon et al. |
| 6,727,339 B2 | | 4/2004 | Luginsland et al. |
| 6,849,754 B2 | | 2/2005 | Deschler et al. |
| 6,984,683 B2 | | 1/2006 | Luginsland et al. |
| 7,019,160 B2 | | 3/2006 | Korth et al. |
| 7,186,768 B2 | | 3/2007 | Korth et al. |
| 7,323,582 B2 | | 1/2008 | Deschler et al. |
| 7,384,997 B2 | * | 6/2008 | Hasse et al. .................... 524/262 |
| 7,855,248 B2 | * | 12/2010 | Stenzel et al. ................. 524/492 |
| 2004/0266968 A1 | | 12/2004 | Korth et al. |
| 2005/0124740 A1 | | 6/2005 | Klockmann et al. |
| 2006/0160935 A1 | | 7/2006 | Hasse et al. |
| 2006/0161015 A1 | | 7/2006 | Klockmann et al. |
| 2006/0204422 A1 | | 9/2006 | Korth et al. |
| 2006/0204767 A1 | | 9/2006 | Albert et al. |
| 2006/0241224 A1 | | 10/2006 | Krafczyk et al. |
| 2006/0252952 A1 | | 11/2006 | Korth et al. |
| 2007/0049669 A1 | | 3/2007 | Korth et al. |
| 2007/0054056 A1 | | 3/2007 | Albert et al. |
| 2007/0066760 A1 | | 3/2007 | Korth et al. |
| 2007/0203274 A1 | | 8/2007 | Korth et al. |

FOREIGN PATENT DOCUMENTS

| | | |
|---|---|---|
| DE | 21 41 159 | 3/1973 |
| DE | 22 12 239 | 4/1973 |
| DE | 22 55 577 | 6/1974 |
| DE | 24 05 758 | 8/1975 |
| DE | 25 43 535 | 4/1976 |
| DE | 27 12 866 | 9/1978 |
| EP | 784 072 | 7/1997 |
| EP | 1 323 549 | 7/2003 |
| JP | 60033838 | 2/1985 |
| JP | 06240052 | 8/1994 |
| JP | 2002121327 A | 4/2002 |
| WO | WO 2007068555 | 6/2007 |
| WO | WO 2007085521 | 8/2007 |

OTHER PUBLICATIONS

International Preliminary Report on Patentability/Written Opinion.
Berkemeir, D. et al. (2002) "Mixing of Silica Compounds from the View Point of a Manufacturer of Internal Mixers" Gummi, Fasern Kunstsoffe 54(1)17-22.
Pohl, E.R. et al. (1992) "Kinetics of the Hydrolysis and Condensation of Organofunctional Alkoxysilanes: A Review" J. Adhesion Sci. Technol. 6(1):127-149.
Luginsland, Hans-Detlef. (2002) "A Review on the Chemistry and the Reinforcement of the Silica-Silane Filler system for Rubber Applications".
Bayer AG (1991) Hundbuch fur die Gummidustrie (Handbook for the Rubber Industry) 2nd Ed. pp. 360-361.
Bayer AG (1991) Hundbuch fur die Gummidustrie (Handbook for the Rubber Industry) 2nd Ed. pp. 384.
Hofmann, W. (1967) Vulcanization and Vulcanizing Agents. p. 181.
Written Opinion of the International Searching Authority received in PCT/EP2007/050174 mailed Feb. 5, 2007.
International Search Report received in PCT/EP2007/050174 mailed Feb. 5, 2007.
Hofmann, W. (1989) Rubber Technology Handbook. Oxford University Press, New York, NY.

(Continued)

*Primary Examiner* — Margaret Moore
(74) *Attorney, Agent, or Firm* — Smith, Gambrell & Russell, LLP

(57) ABSTRACT

Rubber mixtures, including at least one rubber, a filler, an organosilicon compound of the formula I

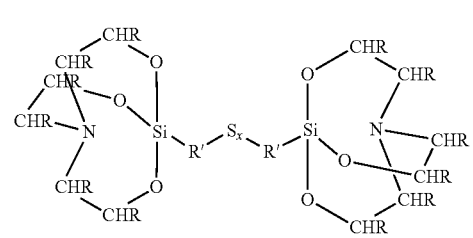

I one rubber accelerator and one co-accelerator. The rubber mixtures are prepared by mixing at least one rubber, a filler, an organosilicon compound of the formula I, one rubber accelerator and one co-accelerator. The rubber mixtures can be used for production of moldings. Also disclosed is a process for preparation of the organosilicon compound of the formula I via transesterification.

11 Claims, 2 Drawing Sheets

OTHER PUBLICATIONS

International Search Report.

Written Opinion.

Page 18, Berkemeier, D.; Hader, W.,; Heiss, G.; "Mixing of Silica Compounds from the View Point of a Manufacturer of Internal Mixers", Gummi, Fasern Kunststoffe (2002), 54(1).

E.R. Pohl, F.D. Osterholtz J. Adhesion Sci. Technology 6(1) 1992, 127-149.

H.D. Luginsland, "A Review on the Chemistry and the Reinforcement of the Silica-Silane Filler System for Rubber Applications," Shaker Verlag, Aachen 2002—p. 34.

Bayer HG, Hundbuch fur die Gummidustrie (Handbook for the Rubber Industry, 2d Ed., 1991, p. 384.

Werner Hofmann, Vulcanization and Vulcanizing Agents, 1967, p. 181.

Bayer AG, Hundbuch fur die Gummidustrie (Handbook for the Rubber Industry, 2d Ed., 1991, pp. 360-361.

"Rubber Technology Handbook", W. Hofmann, Hanser Verlag 1994.

List of Related Cases.

* cited by examiner

RUBBER MIXTURES

INTRODUCTION AND BACKGROUND

The invention relates to rubber mixtures, to their preparation and to their use.

It is known that hydrolysable sulphur-containing organosilicon compounds are capable of reacting with fillers containing hydroxy groups, e.g. natural and synthetic silicates, carbonates, glasses and metal oxides. They are used here for surface modification and to promote adhesion. The rubber-processing industry uses them as coupling agents between the reinforcing filler and the polymer used (DE2141159, DE2212239, DE19544469A1, U.S. Pat. No. 3,978,103, U.S. Pat. No. 4,048,206, EP784072A1).

It is moreover known that the use of commercially available silane coupling agents having three alkyloxy substituents on the silicon atom (DE 22 55 577), e.g. bis[3-triethoxysilylpropyl]tetrasulphide or bis[3-triethoxysilylpropyl] disulphide leads to liberation of considerable amounts of alcohol during and after coupling to the filler. Since trimethoxy- and triethoxy-substituted silanes are generally used, the corresponding alcohols methanol and ethanol are liberated in the course of the application (e.g. page 18 in Berkemeier, D.; Hader, W.; Rinker, M.; Heiss, G., Mixing of silica compounds from the viewpoint of a manufacturer of internal mixers, Gummi, Fasern, Kunststoffe (2001), 54(1), 17-22).

It is moreover known that methoxy-substituted silanes have higher hydrolysis-activity than ethoxy-substituted silanes. Ethoxy-substituted silanes have higher hydrolysis-activity than longer-chain or branched alkoxy-substituted silanes having more than 2 carbon atoms (E. R. Pohl, F. D. Osterholtz *J. Adhesion Sci. Technology* 6(1) 1992, 127-149). They are therefore capable of faster coupling to the filler, and use of methoxy- and ethoxy-substituted silanes has therefore hitherto been essential for economic reasons.

A considerable disadvantage in the use of known alkoxy silane coupling agents, specifically of bis(trialkoxysilylalkyl) polysulphide coupling agents, is the liberation of stoichiometric amounts of volatile alcohols, such as methanol and ethanol, into the environment during and after coupling of the alkoxysilane to the filler.

Another disadvantage in the use of bis(triethoxysilylpropyl)polysulphide coupling agents is the limitation on mixing temperature for rubber mixtures to the temperature range from 140 to 165° C. (H. D Luginsland, "A Review on the chemistry and the reinforcement of the silica-silane filler system for rubber applications, Shaker Verlag, Aachen 2002, page 34).

U.S. Pat. No. 6,433,206, DE 25 42 534 C3, DE 24 05 758 C3 and DE 27 12 866 A1 disclose polysulphide-containing silatranes. They can be used as reinforcing additives in rubber mixtures comprising silicatic fillers.

SUMMARY OF THE INVENTION

It is an object of the present inventions to provide rubber mixtures which, with small amounts of co-accelerator, exhibit very good vulcanization behaviour.

The invention provides rubber mixtures, comprising
(a) at least one rubber,
(b) a filler,
(c) an organosilicon compound of general formula I,

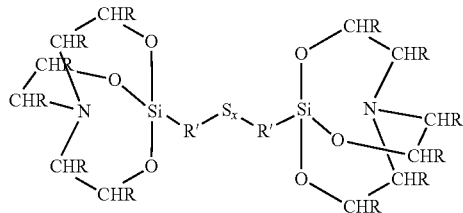

where R is identical or different and is H, a cyclic, straight-chain or branched $C_1$-$C_{12}$-alkyl, preferably $C_1$-$C_8$-alkyl, particularly preferably $C_1$-alkyl, a carboxy group (—COOH), a substituted or unsubstituted aryl group, preferably a phenyl group or a substituted or unsubstituted aralkyl group, R' is identical or different and is a branched or unbranched, saturated or unsaturated, aliphatic, aromatic or mixed aliphatic/aromatic divalent $C_1$-$C_{30}$, preferably $C_1$-$C_{20}$, particularly preferably $C_2$-$C_{20}$, very particularly preferably $C_3$-$C_{15}$, extremely preferably $C_4$-$C_{15}$, hydrocarbon group, x is an average chain length of from 1 to 10, (d) from 0.3 to 5% by weight, preferably from 0.3 to 4% by weight, particularly preferably from 0.3 to 3% by weight, very particularly preferably from 0.5 to 2.5% by weight, of rubber accelerator, based on the rubber used, selected from the group of the thiazoles, sulphenamides, thiurams, thioureas, thiocarbonates and dithiocarbamates and (e) an amount equal to or less than 1.5% by weight, preferably less than 1% by weight, particularly preferably less than 0.5% by weight, based on the rubber used, of co-accelerator, selected from the group of the guanidines and aldehydamines.

DETAILED DESCRIPTION OF INVENTION

Figure 1:
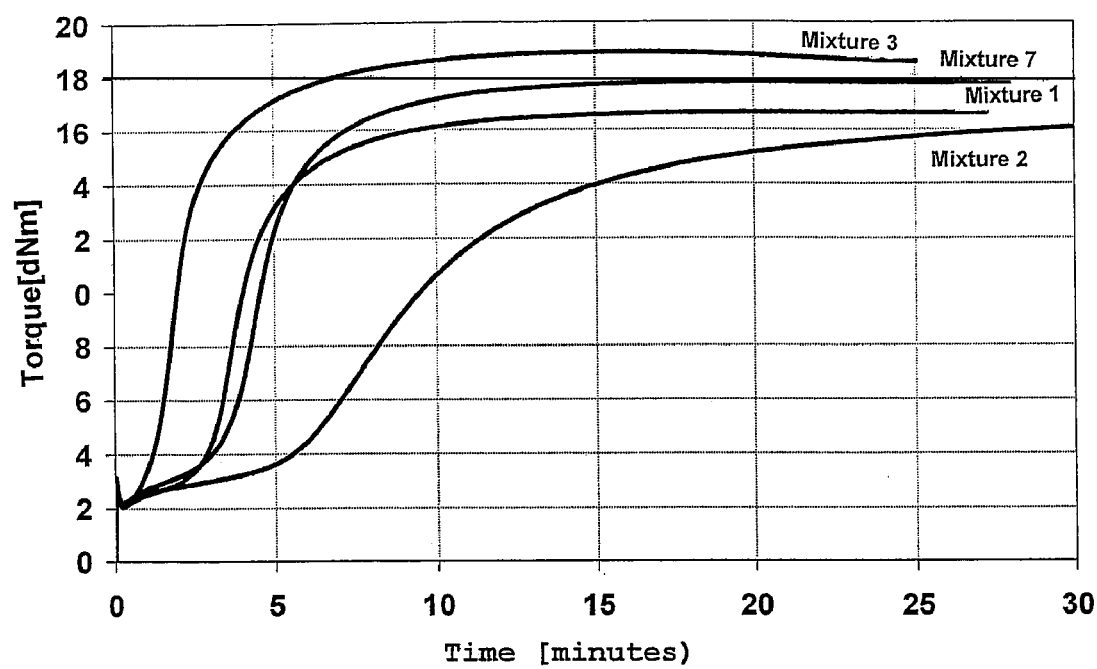
FIG. 1 shows the vulcameter curves for mixtures 1, 2, 3 and 7.

In one embodiment, the rubber mixture can comprise no co-accelerator.

In another embodiment, the rubber mixture can comprise from 0.1 to 1% by weight of co-accelerator.

The amounts that can be used of the organosilicon compounds of the formula I can be from 0.1 to 50% by weight, preferably from 0.1 to 25% by weight, particularly preferably from 1 to 15% by weight, very particularly preferably from 3 to 10% by weight, based on the amount of the rubber used (phr).

R' can be $CH_2$, $CH_2CH_2$, $CH_2CH_2CH_2$, $CH_2CH_2CH_2CH_2$, $CH(CH_3)$, $CH_2CH(CH_3)$, $CH(CH_3)CH_2$, $C(CH_3)_2$, $CH(C_2H_5)$, $CH_2CH_2CH(CH_3)$, $CH(CH_3)CH_2CH_2$, $CH_2CH(CH_3)CH_2$ or

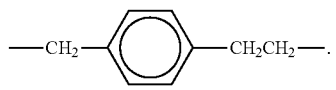

Organosilicon compounds of the general formula I can be mixtures composed of organosilicon compounds of the general formula I.

Organosilicon compounds of the general formula I can be mixtures composed of organosilicon compounds of the general formula I which have different values of x.

The index x here is the average sulphur chain length in the mixture of substances and can be from 1.1 to 5, preferably from 1.5 to 4.5, particularly preferably from 3 to 4 and, respectively, from 1.8 to 3, very particularly preferably from 3.5 to 3.8 and, respectively, from 1.9 to 2.6. The proportion of S2 compounds in mixtures of the organosilicon compounds of the general formula I can be more than 50% by weight, preferably more than 60% by weight, particularly preferably more than 70% by weight, very particularly preferably more than 80% by weight, based on the amount of organosilicon compound used of the general formula I. The proportion of S3 compounds in mixtures of the organosilicon compounds of the general formula I can be from 0.5 to 60% by weight, preferably from 1 to 50% by weight, particularly preferably from 1 to 45% by weight, very particularly preferably from 1 to 40% by weight, based on the amount of organosilicon compound used of the general formula I. The proportion of S4 compounds in mixtures of the organosilicon compounds of the general formula I can be more than 0.5% by weight, preferably more than 5% by weight, particularly preferably more than 9% by weight, very particularly preferably more than 15% by weight, extremely preferably more than 25% by weight, based on the amount of organosilicon compound used of the general formula I.

Organosilicon compounds of the formula I can be
[N($C_2H_4O$)$_3$Si($CH_2$)$_3$]$S_2$[($CH_2$)$_3$Si($OC_2H_4$)$_3$N],
[N($C_2H_4O$)$_3$Si($CH_2$)$_3$]$S_3$[($CH_2$)$_3$Si($OC_2H_4$)$_3$N],
[N($C_2H_4O$)$_3$Si($CH_2$)$_3$]$S_4$[($CH_2$)$_3$Si($OC_2H_4$)$_3$N],
[N($C_2H_4O$)$_3$Si($CH_2$)$_3$]$S_5$[($CH_2$)$_3$Si($OC_2H_4$)$_3$N],
[N($C_2H_4O$)$_3$Si($CH_2$)$_2$]$S_2$[($CH_2$)$_2$Si($OC_2H_4$)$_3$N],
[N($C_2H_4O$)$_3$Si($CH_2$)$_2$]$S_3$[($CH_2$)$_2$Si($OC_2H_4$)$_3$N],
[N($C_2H_4O$)$_3$Si($CH_2$)$_2$]$S_4$[($CH_2$)$_2$Si($OC_2H_4$)$_3$N],
[N($C_2H_4O$)$_3$Si($CH_2$)$_2$]$S_5$[($CH_2$)$_2$Si($OC_2H_4$)$_3$N],
[N($C_2H_4O$)$_3$Si($CH_2$)]$S_2$[($CH_2$)Si($OC_2H_4$)$_3$N],
[N($C_2H_4O$)$_3$Si($CH_2$)]$S_3$[($CH_2$)Si($OC_2H_4$)$_3$N],
[N($C_2H_4O$)$_3$Si($CH_2$)]$S_4$[($CH_2$)Si($OC_2H_4$)$_3$N],
[N($C_2H_4O$)$_3$Si($CH_2$)]$S_5$[($CH_2$)Si($OC_2H_4$)$_3$N],
[N($C_2H_4O$)$_3$Si—$CH_2CH_2CH(CH_3)$—]$S_2$[—CH($CH_3$)$CH_2CH_2$—Si($OC_2H_4$)$_3$N],
[N($C_2H_4O$)$_3$Si—$CH_2CH_2CH(CH_3)$—]$S_3$[—CH($CH_3$)$CH_2CH_2$—Si($OC_2H_4$)$_3$N],
[N($C_2H_4O$)$_3$Si—$CH_2CH_2CH(CH_3)$—]$S_4$[—CH($CH_3$)$CH_2CH_2$—Si($OC_2H_4$)$_3$N],
[N($C_2H_4O$)$_3$Si—$CH_2CH_2CH(CH_3)$—]$S_5$[—CH($CH_3$)$CH_2CH_2$—Si($OC_2H_4$)$_3$N],
[N($CH_2$—CH(Me)—O—)$_3$Si($CH_2$)$_3$]$S_2$[($CH_2$)$_3$Si(—O—CH(Me)—$CH_2$)$_3$N],
[N($CH_2$—CH(Me)—O—)$_3$Si($CH_2$)$_3$]$S_3$[($CH_2$)$_3$Si(—O—CH(Me)—$CH_2$)$_3$N],
[N($CH_2$—CH(Me)—O—)$_3$Si($CH_2$)$_3$]$S_4$[($CH_2$)$_3$Si(—O—CH(Me)—$CH_2$)$_3$N]
[N($CH_2$—CH(Me)—O—)$_3$Si($CH_2$)$_3$]$S_5$[($CH_2$)$_3$Si(—O—CH(Me)—$CH_2$)$_3$N]
[N($CH_2$—CH(Me)—O—)$_3$Si($CH_2$)$_2$]$S_2$[($CH_2$)$_2$Si(—O—CH(Me)—$CH_2$)$_3$N],
[N($CH_2$—CH(Me)—O—)$_3$Si($CH_2$)$_2$]$S_3$[($CH_2$)$_2$Si(—O—CH(Me)—$CH_2$)$_3$N],
[N($CH_2$—CH(Me)—O—)$_3$Si($CH_2$)$_2$]$S_4$[($CH_2$)$_2$Si(—O—CH(Me)—$CH_2$)$_3$N],
[N($CH_2$—CH(Me)—O—)$_3$Si($CH_2$)$_2$]$S_5$[($CH_2$)$_2$Si(—O—CH(Me)—$CH_2$)$_3$N],
[N($CH_2$—CH(Me)—O—)$_3$Si($CH_2$)]$S_2$[($CH_2$)Si(—O—CH(Me)—$CH_2$)$_3$N],
[N($CH_2$—CH(Me)—O—)$_3$Si($CH_2$)]$S_3$[($CH_2$)Si(—O—CH(Me)—$CH_2$)$_3$N],
[N($CH_2$—CH(Me)—O—)$_3$Si($CH_2$)]$S_4$[($CH_2$)Si(—O—CH(Me)—$CH_2$)$_3$N],
[N($CH_2$—CH(Me)—O—)$_3$Si($CH_2$)]$S_5$[($CH_2$)Si(—O—CH(Me)—$CH_2$)$_3$N],
[N($CH_2$—CH(Me)—O—)$_3$Si—$CH_2CH_2CH(CH_3)$—]$S_2$[—CH($CH_3$)$CH_2CH_2$—Si(—O—CH(Me)—$CH_2$)$_3$N],
[N($CH_2$—CH(Me)—O—)$_3$Si—$CH_2CH_2CH(CH_3)$—]$S_3$[—CH($CH_3$)$CH_2CH_2$—Si(—O—CH(Me)—$CH_2$)$_3$N],
[N($CH_2$—CH(Me)—O—)$_3$Si—$CH_2CH_2CH(CH_3)$—]$S_4$[—CH($CH_3$)$CH_2CH_2$—Si(—O—CH(Me)—$CH_2$)$_3$N],
[N($CH_2$—CH(Me)—O—)$_3$Si—$CH_2CH_2CH(CH_3)$—]$S_5$[—CH($CH_3$)$CH_2CH_2$—Si(—O—CH(Me)—$CH_2$)$_3$N],
[N($CH_2$—CH(phenyl)-O—)$_3$Si($CH_2$)$_3$]$S_2$[($CH_2$)$_3$Si(—O—CH(phenyl)-$CH_2$)$_3$N],
[N($CH_2$—CH(phenyl)-O—)$_3$Si($CH_2$)]$S_3$[($CH_2$)$_3$Si(—O—CH(phenyl)-$CH_2$)$_3$N],
[N($CH_2$—CH(phenyl)-O—)$_3$Si($CH_2$)$_3$]$S_4$[($CH_2$)$_3$Si(—O—CH(phenyl)-$CH_2$)$_3$N],
[N($CH_2$—CH(phenyl)-O—)$_3$Si($CH_2$)$_3$]$S_5$[($CH_2$)$_3$Si(—O—CH(phenyl)-$CH_2$)$_3$N],
[N($CH_2$—CH(phenyl)-O—)$_3$Si($CH_2$)$_2$]$S_2$[($CH_2$)$_2$Si(—O—CH(phenyl)-$CH_2$)$_3$N],
[N($CH_2$—CH(phenyl)-O—)$_3$Si($CH_2$)$_2$]$S_3$[($CH_2$)$_2$Si(—O—CH(phenyl)-$CH_2$)$_3$N],
[N($CH_2$—CH(phenyl)-O—)$_3$Si($CH_2$)$_2$]$S_4$[($CH_2$)$_2$Si(—O—CH(phenyl)-$CH_2$)$_3$N],
[N($CH_2$—CH(phenyl)-O—)$_3$Si($CH_2$)$_2$]$S_5$[($CH_2$)$_2$Si(—O—CH(phenyl)-$CH_2$)$_3$N],
[N($CH_2$—CH(phenyl)-O—)$_3$Si($CH_2$)]$S_2$[($CH_2$)Si(—O—CH(phenyl)-$CH_2$)$_3$N],
[N($CH_2$—CH(phenyl)-O—)$_3$Si($CH_2$)]$S_3$[($CH_2$)Si(—O—CH(phenyl)-$CH_2$)$_3$N],
[N($CH_2$—CH(phenyl)-O—)$_3$Si($CH_2$)]$S_4$[($CH_2$) Si(—O—CH(phenyl)-$CH_2$)$_3$N],
[N($CH_2$—CH(phenyl)-O—)$_3$Si($CH_2$)]$S_5$[($CH_2$) Si(—O—CH(phenyl)-$CH_2$)$_3$N],
[N($CH_2$—CH(phenyl)-O—)$_3$Si—$CH_2CH_2CH(CH_3)$—]$S_2$[—CH($CH_3$)$CH_2CH_2$—Si(—O—CH(phenyl)-$CH_2$)$_3$N],
[N($CH_2$—CH(phenyl)-O—)$_3$Si—$CH_2CH_2CH(CH_3)$—]$S_3$[—CH($CH_3$)$CH_2CH_2$—Si(—O—CH(phenyl)-$CH_2$)$_3$N],
[N($CH_2$—CH(phenyl)-O—)$_3$Si—$CH_2CH_2CH(CH_3)$—]$S_4$[—CH($CH_3$)$CH_2CH_2$—Si(—O—CH(phenyl)-$CH_2$)$_3$N]
or
[N($CH_2$—CH(phenyl)-O—)$_3$$S_1$—$CH_2CH_2CH(CH_3)$—]$S_5$[—CH($CH_3$)$CH_2CH_2$—Si(—O—CH(phenyl)-$CH_2$)$_3$N].

Condensates, i.e. oligo- and polysiloxanes, can be formed from the organosilicon compounds of the formula I via addition of water. The oligo- and polysiloxanes can be obtained via oligomerization or co-oligomerization of the corresponding organosilicon compounds of the general formula I via addition of water using the procedure and additive addition known to the person skilled in the art in this field.

The organosilicon compounds of the formula I can also be mixtures of organosilicon compounds of the general formula I with mixtures of oligomeric or polymeric siloxanes of the organosilicon compounds of the general formula I.

The constitution of the mixtures of the organosilicon compounds of the general formula I can be determined via nuclear magnetic resonance spectroscopy, preferably via $^1$H-, $^{13}$C- and $^{29}$Si-nuclear magnetic resonance spectroscopy. The average —$S_x$— chain length in the mixtures of the inventive organosilicon compounds can preferably be determined via $^1$H nuclear magnetic resonance spectroscopy.

The organosilicon compounds of the formula I can have a molar ratio (N/S) between the analytically determinable content of nitrogen (N) and sulphur (S) of from 2 (2/1) to 0.2 (2/10), preferably from 1.33 (2/1.5) to 0.5 (2/4), particularly preferably from 1.11 (2/1.8) to 0.66 (2/3), very particularly preferably from 1.05 (2/1.9) to 0.8 (2/2.5).

The average sulphur content can be determined analytically using equipment from LECO (LECO SC-144 DR), using ASTM 6741-01 method B.

The average nitrogen content can be determined by the Kjeldahl method, or by using an elemental analyser, such as Carlo Erba EA 1108 (combustion of substance and determination of $N_2$).

The melting point of the inventive organic silicon compounds, determinable via differential scanning calorimetry (DSC), can be from 50° C. to 200° C., preferably from 70° C. to 180° C., particularly preferably from 90° to 170° C., very particularly preferably from 110° C. to 160° C.

The melting point can be defined as the peak of the melting curve.

The melting range of the mixtures of organosilicon compounds, determinable via differential scanning calorimetry, can be from 30° C. to 220° C., preferably from 50° C. to 200° C., particularly preferably from 70° to 180° C., very particularly preferably from 90° C. to 180° C.

The melting range can be defined as the temperature range between peak-start temperature and peak-end temperature during a DSC measurement.

The organosilicon compounds of the general formula I can comprise, as ancillary components, amounts of less than 10% by weight, preferably less than 8% by weight, particularly preferably less than 5% by weight, very particularly preferably less than 3% by weight, of compounds which have silicon atoms substituted by alkyloxy groups (alkyl-O—).

The organosilicon compounds of the general formula I can comprise less than 15% by weight, preferably less than 12% by weight, particularly preferably less than 8% by weight, very particularly preferably less than 5% by weight, of compounds of the general formula II

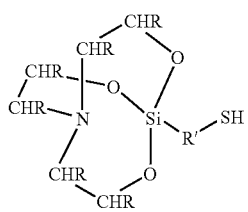

II where R and R' are as defined above.

The organosilicon compounds used of the general formula I can comprise less than 10% by weight, preferably less than 8% by weight, particularly preferably less than 5% by weight, very particularly preferably less than 3% by weight, of chloride ions (Cl⁻).

The form in which the organosilicon compounds of the formula I are added to the mixing process can either be pure form or else absorbed onto an inert organic or inorganic carrier, or else pre-reacted with an organic or inorganic carrier. Preferred carrier materials can be precipitated or fumed silicas, waxes, thermoplastics, natural or synthetic silicates, natural or synthetic oxides, such as aluminium oxide, or carbon blacks. Another form in which the organosilicon compounds of the formula I can be added to the mixing process is pre-reacted with the filler to be used.

Preferred waxes can be waxes with melting points, melting ranges or softening ranges of from 50° to 200° C., preferably from 70° to 180° C., particularly preferably from 90° to 150° C., very particularly preferably from 1000 to 120° C.

The waxes used can be olefinic waxes.

The waxes used can contain saturated and unsaturated hydrocarbon chains.

The waxes used can comprise polymers or oligomers, preferably emulsion SBR or/and solution SBR.

The waxes used can comprise long-chain alkanes or/and long-chain carboxylic acids.

The waxes used can comprise ethylene-vinyl acetate and/or polyvinyl alcohols.

A form in which the organosilicon compounds of the formula I can be added to the mixing process is a physical mixture with an organic substance or with an organic substance mixture.

The organic substance or the organic substance mixture can comprise polymers or oligomers.

Polymers or oligomers can be heteroatom-containing polymers or oligomers, e.g. ethylene-vinyl alcohol or/and polyvinyl alcohols.

Polymers or oligomers can be saturated or unsaturated elastomers, preferably emulsion SBR or/and solution SBR.

The melting point, melting range or softening range of the mixture composed of organosilicon compounds of the formula I and of organic substance or of an organic substance mixture can be from 50 to 200° C., preferably from 70 to 180° C., particularly preferably from 70 to 150° C., very particularly preferably from 70 to 130° C., extremely preferably from 90 to 110° C.

Fillers that can be used for the inventive rubber mixtures are:

Carbon blacks, such as flame blacks, furnace blacks, gas blacks or thermal blacks. The BET surface areas of the carbon blacks can be from 20 to 200 m²/g. The carbon blacks can, if appropriate, also contain heteroatoms, such as Si.

Amorphous silicas, prepared by way of example via precipitation of solutions of silicates (precipitated silicas) or flame hydrolysis of silicon halides (fumed silicas). The surface areas of the silicas can be from 5 to 1000 m²/g, preferably from 20 to 400 m²/g (BET surface area) and their primary particle sizes can be from 10 to 400 nm. The silicas can, if appropriate, also take the form of mixed oxides with other metal oxides, such as Al oxides, Mg oxides, Ca oxides, Ba oxides, Zn oxides and titanium oxides.

Synthetic silicates, such as aluminium silicate, alkaline earth metal silicates, such as magnesium silicate or calcium silicate, with BET surface areas of from 20 to 400 m²/g and with primary particle diameters of from 10 to 400 nm.

Synthetic or natural aluminium oxides and synthetic or natural aluminium hydroxides.

Synthetic or natural calcium carbonates, e.g. precipitated calcium carbonat.

Natural silicates, such as kaolin and other naturally occurring silicas.

Glass fibre and glass fibre products (mats, strands) or glass microbeads.

It may be preferable to use amorphous silicas prepared via precipitation of solutions of silicates (precipitated silicas) with BET surface areas of from 20 to 400 m²/g. The amounts that can be used of the amorphous silicas are from 5 to 150 parts by weight, based in each case on 100 parts of rubber (phr).

The fillers mentioned can be used alone or in a mixture. In one particularly preferred embodiment, the rubber mixtures can comprise from 10 to 150 parts by weight of pale-coloured fillers, if appropriate together with from 0 to 100 parts by weight of carbon black, and also from 1 to 20 parts by weight or organosilicon compounds of the formula I, based in each case on 100 parts by weight of rubber.

Suitable materials for preparation of the inventive rubber mixtures are not only natural rubber but also synthetic rubbers. Preferred synthetic rubbers are described by way of example in W. Hofmann, Kautschuktechnologie [Rubber technology], Genter Verlag, Stuttgart 1980. Synthetic rubbers that can be used are, inter alia polybutadiene (BR);
polyisoprene (IR);
styrene-butadiene copolymers (SBR), such as emulsion SBR (E-SBR) or solution SBR (S-SBR). The styrene-butadiene copolymers can have styrene content of from 1 to 60% by weight, preferably from 2 to 50% by weight, particularly preferably from 10 to 40% by weight, very particularly preferably from 15 to 35% by weight;
chloroprene (CR);
isobutylene-isoprene copolymers (IIR);
butadiene-acrylonitrile copolymers whose acrylo-nitrile contents are from 5 to 60% by weight, preferably from 10 to 50% by weight (NBR), particularly preferably from 10 to 45% by weight (NBR), very particularly preferably from 19 to 45% by weight (NBR);
partially hydrogenated or fully hydrogenated NBR rubber (HNBR);
ethylene-propylene-diene copolymers (EPDM);
abovementioned rubbers which also have functional groups, e.g. carboxy groups, silanol groups or epoxy groups, e.g. epoxidized NR, carboxy-functionalized NBR or silanol-(—SiOH) or silyl-alkoxy-functionalized (—Si—OR) SBR;

or a mixture of these rubbers. Anionically polymerized SSBR rubbers (solution SBR) whose glass transition temperature is above −50° C. and their mixtures with diene rubbers are of particular interest for production of car tyre treads.

The inventive rubber mixtures can comprise other rubber auxiliaries, such as reaction accelerators, antioxidants, heat stabilizers, light stabilizers, anti-ozonants, processing aids, plasticizers, tackifiers, blowing agents, dyes, pigments, waxes, extenders, organic acids, retarders, metal oxides, and also activators, such as triethanolamine or hexanetriol.

Other rubber auxiliaries can be: polyethylene glycol or/and polypropylene glycol or/and polybutylene glycol with molar masses from 50 to 50 000 g/mol, preferably from 50 to 20 000 g/mol, particularly preferably from 200 to 10 000 g/mol, very particularly preferably from 400 to 6000 g/mol, extremely preferably from 500 to 3000 g/mol,
hydrocarbon-terminated polyethylene glycol
Alk-O—$(CH_2—CH_2—O)_{y'}$—H or Alk-$(CH_2—CH_2—O)_{y'}$-Alk,
hydrocarbon-terminated polypropylene glycol
Alk-O—$(CH_2—CH(CH_3)—O)_{y'}$—H or Alk-O—$(CH_2—CH(CH_3)—O)_{y'}$-Alk,
hydrocarbon-terminated polybutylene glycol
Alk-O—$(CH_2—CH_2—CH_2—CH_2—O)_{y'}$—H,
Alk-O—$(CH_2—CH(CH_3)—CH_2—O)_{y'}$—H,
Alk-O—$(CH_2—CH_2—CH_2—CH_2—O)_{y'}$-Alk or
Alk-O—$(CH_2—CH(CH_3)—CH_2—O)_{y'}$-Alk,
where the average of $y'$ is from 2 to 25, preferably from 2 to 15, particularly preferably from 3 to 8 and from 10 to 14, very particularly preferably from 3 to 6 and from 10 to 13, and Alk is a branched or unbranched, unsubstituted or substituted, saturated or unsaturated hydrocarbon having from 1 to 35, preferably from 4 to 25, particularly preferably from 6 to 20, very particularly preferably from 10 to 20, extremely preferably from 11 to 14, carbon atoms,
neopentyl glycol HO—$CH_2$—$C(Me)_2$-$CH_2$—OH, pentaerythritol $C(CH_2$—$OH)_4$ or trimethylolpropane $CH_3$—$CH_2$—$C(CH_2$—$OH)_3$ etherified with polyethylene glycol, etherified with polypropylene glycol, etherified with polybutylene glycol, or etherified with a mixture thereof, where the number of repeat units of ethylene glycol, propylene glycol or/and butylene glycol in the etherified polyalcohols can be from 2 to 100, preferably from 2 to 50, particularly preferably from 3 to 30, very particularly preferably from 3 to 15.

To calculate the average of $y'$, the analytically determinable amount of polyalkylene glycol units can be divided by the analytically determinable amount of -Alk [(amount of polyalkylene glycol units)/(amount of -Alk)]. By way of example, $^1H$ and $^{13}C$ nuclear magnetic resonance spectroscopy can be used to determine the amounts.

The amounts used of the rubber auxiliaries can be known amounts, oriented inter alia to the intended purpose. As a function of the processing aid used, amounts can be from 0.001 to 50% by weight, preferably from 0.001 to 30% by weight, particularly preferably from 0.01 to 30% by weight, very particularly preferably from 0.1 to 30% by weight, based on rubber (phr).

The inventive rubber mixtures can be sulphur-vulcanizable rubber mixtures.

The inventive rubber mixtures can be peroxidically crosslinkable rubber mixtures.

Crosslinking agents used can be sulphur or sulphur-donor substances. The amounts of sulphur used can be from 0.1 to 10% by weight, preferably from 0.1 to 5% by weight, based on rubber.

The following substances can be used as rubber accelerator: 2-mercaptobenzothiazole, dibenzothiazyl disulphide, zinc mercaptobenzothiazole, 2-(morpholino-thio)benzothiazole, diisopropylbenzothiazylsulphenamide, N-cyclohexyl-2-benzothiazylsulphenamide, N,N-dicyclohexyl-2-benzothiazylsulphenamide, N-tert-butyl-2-benzothiazylsulphenamide, benzothiazyl-2-sulphenomorpholide, N-dicyclohexyl-2-benzothiazylsulphenamide, tetramethylthiuram monosulphide, tetramethylthiuram disulphide, tetraethylthiuram disulphide, tetrabutylthiuram disulphide, tetra-benzylthiuram disulphide, tetraisobutylthiuram disulphide, N,N'-dimethyl-N,N'-diphenylthiuram disulphide, dipentamethylenethiuram disulphide, dipentamethylenethiuram tetra/hexasulphide, N,N'-ethyl-thiourea, N,N'-diethylthiourea, N,N'-diphenylthiourea, N'-(3,4-dichlorophenyl)-N,N'-dimethylthiourea, N,N'-dibutylthiourea, N,N,N'-tributylthiourea, zinc dimethyldithiocarbamate, zinc diethyldithiocarbamate, zinc dibutyldithiocarbamate, zinc diisobutyldithiocarbamate, zinc dibenzyldithiocarbamate, zinc ethyl-phenyldithiocarbamate, zinc pentamethylenedithio-carbamate, zinc diisononyldithiocarbamate, zinc diamyldithiocarbamate, tellurium diethyldithiocarbamate, copper dimethyldithiocarbamate, copper dibutyldithiocarbamate, bismuth dimethyldithio-carbamate, cadmium diethyldithiocarbamate, selenium diethyldithiocarbamate, piperidine pentamethylene-dithiocarbamate, nickel dimethyldithiocarbamate, nickel diethyldithiocarbamate, nickel dibutyldithiocarbamate, nickel diisobutyldithiocarbamate, nickel dibenzyldithiocarbamate, lead diamyldithiocarbamate, sodium dimethyldithiocarbamate, sodium diethyldithiocarbamate, sodium dibutyldithiocarbamate, sodium diisobutyldithiocarbamate or sodium dibenzyldithiocarbamate.

The co-accelerator used can comprise diphenylguanidine, di-o-tolylguanidine, o-tolylbiguanidine, N,N'-diphenylguanidine, hexamethylenetetramine, condensates of homologous acroleins with aromatic bases or condensates of aldehydes with amines.

The invention also provides a process for preparation of the organosilicon compounds of the formula I, characterized in that organosilicon compounds of the general formula III

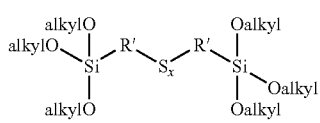

in which R' is as defined above and alkyl is identical or different and is a monovalent C1-C8 hydrocarbon radical, preferably methyl, ethyl and propyl, are reacted with compounds of the general formula IV

N(CHR—CHR—O—H)$_3$    IV in which R is as defined above, with elimination of alkyl-OH, and alkyl-OH is removed from the reaction mixture.

The inventive process for preparation of the organosilicon compounds can take place with or without catalysis. The alkyl-OH can be removed continuously or batchwise from the reaction mixture.

A high monomer content (e.g. detectable via $^{29}$Si NMR or HPLC) of the compounds of the formula III used as starting material can have a favourable effect on the product constitution and the product properties of the organosilicon compounds. A high monomer content corresponds to a low content of siloxanes which have Si—O—Si bonds and which have been formed via hydrolysis from the alkoxysilanes of the formula III with alkyl-OH alcohol elimination. The monomer content of the compounds of the formula III in the starting material can preferably be greater than 50% by weight, particularly preferably greater than 75% by weight, very particularly preferably greater than 85% by weight, extremely preferably greater than 92.5% by weight.

The organosilicon compounds of the general formula III can be pure compounds or mixtures of compounds.

Examples of compounds of the general formula IV can be triethanolamine N(CH$_2$—CH$_2$—O—H)$_3$, triisopropanolamine N(CH$_2$—CH(CH$_3$)—O—H)$_3$ or [HO—CH(phenyl)CH$_2$]$_3$N.

A low water content of the compounds of the formula IV used can have a favourable effect on the constitution and the product properties of the organosilicon compounds. The water content can preferably be smaller than 5% by weight, particularly preferably smaller than 1.5% by weight, very particularly preferably smaller than 0.75% by weight, extremely preferably smaller than 0.3% by weight.

Metal-free or metal-containing catalysts can be used as catalyst in the inventive process.

Alkali metal hydroxides can be used as catalyst in the inventive process. Preferred alkali metal hydroxides can be LiOH, NaOH, KOH and CsOH.

Alkoxides can be used as catalyst in the inventive process. Preferred alkoxides can be alkali metal alkoxides and aluminium alkoxides. Preferred alkali metal alkoxides can be LiOMe and LiOEt, NaOMe, NaOEt, NaOC$_3$H$_7$, KOMe, KOEt and KOC$_3$H$_7$.

Compounds of the 3rd-7th group, of the 13th-14th group and/or the lanthanoids group can be used as metal-containing catalysts.

Transition metal compounds can be used as metal-containing catalysts.

The metal-containing catalysts can be metal compounds, such as metal chlorides, metal oxides, metal oxychlorides, metal sulphides, metal sulphochlorides, metal alcoholates, metal thiolates, metal oxyalcoholates, metal amides, metal imides or transition metal compounds having multiple bonded ligands.

By way of example, metal compounds that can be used are halides, amides, or alcoholates of the 3rd main group ($M^{3+}$= B, Al, Ga, In, Tl:$M^{3+}$(OMe)$_3$, $M^{3+}$(OEt)$_3$, $M^{3+}$(OC$_3$H$_7$)$_3$, $M^{3+}$(OC$_4$H$_9$)$_3$), halides, oxides, sulphides, imides, alcoholates, amides, thiolates and combinations of the substituent classes mentioned having multiple bonded ligands on compounds of the lanthanoids group (rare earths, atomic number from 58 to 71 in the Periodic Table of the Elements), halides, oxides, sulphides, imides, alcoholates, amides, thiolates and combinations of the substituent classes mentioned having multiple bonded ligands on compounds of the 3rd transition group ($M^{3+}$=Sc, Y, La:$M^{3+}$(OMe)$_3$, $M^{3+}$(OEt)$_3$, $M^{3+}$(OC$_3$H$_7$)$_3$, $M^{3+}$(OC$_4$H$_9$)$_3$, cp$M^{3+}$(Cl)$_2$, cp cp$M^{3+}$(OMe)$_2$, cp$M^{3+}$(OEt)$_2$, cp$M^{3+}$(NMe$_2$)$_2$ where cp=cyclopentadienyl), halides, sulphides, amides, thiolates or alcoholates of the 4th main group ($M^{4+}$=Si, Ge, Sn, Pb:$M^{4+}$(OMe)$_4$, $M^{4+}$(OEt)$_4$, $M^{4+}$(OC$_3$H$_7$)$_4$, $M^{4+}$(OC$_4$H$_9$)$_4$; $M^{2+}$=Sn, Pb:$M^{2+}$(OMe)$_2$, $M^{2+}$(OEt)$_2$, $M^{2+}$(OC$_3$H$_7$)$_2$, $M^{2+}$(OC$_4$H$_9$)$_2$), tin dilaurate, tin diacetate, Sn(OBu)$_2$, halides, oxides, sulphides, imides, alcoholates, amides, thiolates and combinations of the substituent classes mentioned having multiple bonded ligands on compounds of the 4th transition group ($M^{4+}$=Ti, Zr, Hf:$M^{4+}$(F)$_4$, $M^{4+}$(Cl)$_4$, $M^{4+}$(Br)$_4$, $M^{4+}$(I)$_4$, $M^{4+}$(OMe)$_4$, $M^{4+}$(OEt)$_4$, $M^{4+}$(OC$_3$H$_7$)$_4$, $M^{4+}$(OC$_4$H$_9$)$_4$, cp$_2$Ti(Cl)$_2$, cp$_2$Zr(Cl)$_2$, cp$_2$Hf(Cl)$_2$, cp$_2$Ti(OMe)$_2$, cp$_2$Zr(OMe)$_2$, cp$_2$Hf(OMe)$_2$, cpTi(Cl)$_3$, cpZr(Cl)$_3$, cpHf(Cl)$_3$, cpTi(OMe)$_3$, cpZr(OMe)$_3$, cpHf(OMe)$_3$, $M^{4+}$(NMe$_2$)$_4$, $M^{4+}$(NEt$_2$)$_4$, $M^{4+}$(NHC$_4$H$_9$)$_4$), halides, oxides, sulphides, imides, alcoholates, amides, thiolates and combinations of the substituent classes mentioned having multiple bonded ligands on compounds of the 5th transition group ($M^{5+}$, $M^{4+}$ or $M^{3+}$=V, Nb, Ta: $M^{5+}$(OMe)$_5$, $M^{5+}$(OEt)$_5$, $M^{5+}$(OC$_3$H$_7$)$_5$, $M^{5+}$(OC$_4$H$_9$)$_5$, $M^{3+}$O(OMe)$_3$, $M^{3+}$O(OEt)$_3$, $M^{3+}$O(OC$_3$H$_7$)$_3$, $M^{3+}$O(OC$_4$H$_9$)$_3$, cpV(OMe)$_4$, cpNb(OMe)$_3$, cpTa(OMe)$_3$, cpV(OMe)$_2$, cpNb(OMe)$_3$, cpTa(OMe)$_3$), halides, oxides, sulphides, imides, alcoholates, amides, thiolates and combinations of the substituent classes mentioned having multiple bonded ligands on compounds of the 6th transition group ($M^{6+}$, $M^{5+}$ or $M^{4+}$=Cr, Mo, W: $M^{6+}$(OMe)$_6$, $M^{6+}$(OEt)$_6$, $M^{6+}$(OC$_3$H$_7$)$_6$, $M^{6+}$(OC$_4$H$_9$)$_6$, $M^{6+}$O(OMe)$_4$, $M^{6+}$O(OEt)$_4$, $M^{6+}$O(OC$_3$H$_7$)$_4$, $M^{6+}$O(OC$_4$H$_9$)$_4$, $M^{6+}$O$_2$(OMe)$_2$, $M^{6+}$O$_2$(OEt)$_2$, $M^{6+}$O$_2$(OC$_3$H$_7$)$_2$, $M^{6+}$O$_2$(OC$_4$H$_9$)$_2$, $M^{6+}$O$_2$(OSiMe$_3$)$_2$) or halides, oxides, sulphides, imides, alcoholates, amides, thiolates and combinations of the substituent classes mentioned having multiple bonded ligands on compounds of the 7th transition group ($M^{7+}$, $M^{6+}$, $M^{5+}$ or $M^{4+}$=Mn, Re:$M^{7+}$O (OMe)$_5$, $M^{7+}$O(OEt)$_5$, $M^{7+}$O(OC$_3$H$_7$)$_5$, $M^{7+}$O(OC$_4$H$_9$)$_5$, $M^{7+}$O$_2$(OMe)$_3$, $M^{7+}$O$_2$(OEt)$_3$, $M^{7+}$O$_2$(OC$_3$H$_7$)$_3$, $M^{7+}$O$_2$(OC$_4$H$_9$)$_3$, $M^{7+}$O$_2$(OSiMe$_3$)$_3$, $M^{7+}$O$_3$(OSiMe$_3$), $M^{7+}$O$_3$(CH$_3$)).

The metal compounds and transition metal compounds can have a free coordination site on the metal.

Other catalysts that can be used are metal compounds and, respectively, transition metal compounds which are formed via addition of water to hydrolysable metal compounds or to hydrolysable transition metal compounds.

By way of example, titanium alkoxides can be used as metal-containing catalysts.

In one particular embodiment, titanium alkoxides such as tetra-n-butyl orthotitanate, tetraethyl orthotitanate, tetra-n-propyl orthotitanate or tetraisopropyl orthotitanate can be used as catalysts.

Organic acids can be used as metal-free catalysts.

Examples of organic acids that can be used are trifluoroacetic acid, trifluoromethanesulphonic acid or p-toluenesulphonic acid, tetraalkylphosphonium halides or trialkylammonium compounds $R_3NH^+X^-$.

Organic bases can be used as metal-free catalysts.

Organic bases that can be used are amines, e.g. alkylamines, dialkylamines or trialkylamines, arylamines, substituted or unsubstituted heterocycles, e.g. DABCO, diisopropylaniline, pyridine or DMAP (4-dimethylaminopyridine).

The inventive process can be carried out at atmospheric pressure or at reduced pressure.

The inventive process can preferably be carried out at from 1 to 600 mbar, particularly preferably at from 5 to 400 mbar, very particularly preferably at from 5 to 200 mbar.

The inventive process can be carried out at temperatures > 25° C.

The inventive process can be carried out in the temperature range from 80° C. to 200° C., preferably from 100° C. to 180° C., particularly preferably from 110° C. to 160° C.

Prior to or during the reaction, the reaction mixture can receive additions of substances which promote transport of water from the product via formation of azeotropic mixtures. The corresponding substances can be cyclic or straight-chain aliphatics, aromatics, mixed aromatic-aliphatic compounds, ethers, alcohols or acids. By way of example, it is possible to use hexane, cyclohexane, benzene, toluene, ethanol, propanol, isopropanol, butanol, ethylene glycol, tetrahydrofuran, dioxane, formic acid, acetic acid, ethyl acetate or dimethylformamide.

The reaction can be carried out continuously or batchwise.

In the inventive process for preparation of the organosilicon compounds of the formula I, the alcohol alkyl-OH corresponding to the substituent (alkyl-O)— in formula III can be used as solvent, the temperature can be from 0 to 100° C., preferably from 10 to 80° C., particularly preferably from 20 to 80° C., and alkali metal hydroxides can be used as catalyst.

An amount of alkali metal hydroxides which is less than 10% by weight, preferably less than 5% by weight, particularly preferably less than 2% by weight, extremely preferably less than 1% by weight, based on the weight of the compound used of the general formula III, can be used as catalyst.

The conduct of the inventive process for preparation of the organosilicon compounds of the formula I can be such that the product obtained comprises a solid that can be filtered from the solvent used, and that the mother liquor produced during the precipitation process is recycled in order to permit use in a fresh reaction to give compounds of the formula I. This can increase the overall yield and reduce the amount of waste.

In the inventive process for preparation of the organosilicon compounds of the formula I, removal of the alcohol alkyl-OH liberated during the transesterification process can take place, via filtration and/or distillation from the resultant product, only after the reaction has ended. The distillation process can preferably be carried out in vacuo and at an elevated temperature, preferably >80° C., particularly preferably >100° C., very particularly preferably >120° C.

In the inventive process, for organosilicon compounds of the general formula I where R is H, R' is (—$CH_2$—$CH_2$—$CH_2$—), x is from 1.5 to 2.8, an alkyl-OH can be used as solvent.

In the inventive process it is possible to add additives prior to, during or after the reaction of the reaction mixture. The additives can preferably be added prior to the reaction. The additives can reduce the alteration induced thermally or by a free-radical route in the average chain length -Sx-.

The additives can be free-radical scavengers and stabilizers known to the person skilled in the art.

The additives can be monofunctional or oligofunctional secondary aromatic amines, monofunctional or oligofunctional substituted phenols or heterocyclic mercaptofunctional compounds.

The additives can be IPPD (N-isopropyl-N'-phenyl-p-phenylenediamine), 6PPD (N-(1,3-dimethylbutyl)-N'-phenyl-p-phenylenediamine), 77PD (N,N'-di(1,4-dimethylpentyl)-p-phenylenediamine), DTPD (a mixture of diaryl-p-phenylenediamines), N,N-diphenyl-p-phenylene-diamine, TMQ (2,2,4-trimethyl-1,2-dihydroquinoline), mixtures of alkylated and aralkylated phenols, SPH (styrenated phenol), BPH (2,2'-methylenebis(4-methyl-6-tert-butylphenol)), sterically hindered phenols, BHT (2,6-di-tert-butyl-4-methylphenol, MBI (2-mercaptobenzimidazole), MMBI (4- and 5-methylmercaptobenzimidazole) or ZMMBI (the zinc salt of 4- or 5-methylmercaptobenzimidazole).

In the inventive process, after the reaction or else as a final step of the process it is possible to add compounds which improve the odour of the product. The substances added can be capable of entering into chemical or physical interactions with sulphur-containing compounds. The compounds added can be epoxy compounds or other substances capable of reactions with inorganic or organic sulphur compounds.

The product of the process can be used as it stands or else after separation to give individual compounds or isolated fractions.

The organosilicon compounds of the formula I can be used as coupling agents between inorganic materials (e.g. glass beads, crushed glass, glass surfaces, glass fibres, metals, oxidic fillers, silicas) and organic polymers (e.g. thermosets, thermoplastics, elastomers) or as crosslinking agents and surface modifiers for oxidic surfaces. The organosilicon compounds of the formula I can be used as coupling reagents in filled rubber mixtures, such as tyre treads.

The organosilicon compounds of the formula I can be prepared and used as solids, powder or pellets, with various particle sizes. Prior to their use they can be milled, sieved, pressed or pelletized, or only certain sieve fractions can be used after sieve separation. The use of certain sieve fractions can be advantageous for processing or rubber properties.

The invention provides a process for preparation of rubber mixtures, characterized in that (a) at least one rubber,
(b) a filler,
(c) an organosilicon compound of general formula I,
(d) from 0 to 5% by weight, preferably from 0 to 4% by weight, particularly preferably from 0 to 3% by weight, very particularly preferably from 0.5 to 2.5% by weight, of rubber accelerator, based on the rubber used, selected from the group of the thiazoles, sulphenamides, thiurams, thioureas, thiocarbonates and dithiocarbamates and
(e) an amount equal to or less than 1.5% by weight, preferably less than 1% by weight, particularly preferably less than 0.5% by weight, based on the rubber used, of co-accelerator, selected from the group of the guanidines and aldehydamines are mixed.

Addition of the organosilicon compounds of the formula I, and also addition of the fillers and additives in the mixing process can take place when the temperatures of the composition are from 90 to 230° C., preferably from 110 to 210° C., particularly preferably from 120 to 190° C. The organosilicon compounds of the formula I can be added together with other rubber auxiliaries.

The mixing of the rubbers with the filler, if appropriate with rubber auxiliaries and with the inventive organosilicon compound can take place in known mixing assemblies, for example on rolls, in internal mixers or in mixing extruders.

The inventive rubber mixtures can be vulcanized at temperatures of from 90 to 230° C., preferably from 110 to 210° C., particularly preferably from 120 to 190° C., if appropriate under a pressure of from 10 to 200 bar.

The inventive rubber mixtures can be used for production of mouldings, e.g. for production of tyres, including pneumatic tyres, tyre treads, cable sheathing, hoses, drive belts, conveyor belts, roll coverings, shoe soles, sealing rings and damping elements.

The inventive rubber mixtures can be prepared at temperatures markedly higher than those for mixtures with the familiar bis(trialkoxysilylalkyl)polysulphide coupling agents, with simultaneous improvement in processing properties and in physical data.

The inventive rubber mixtures have the particular advantage that, despite a marked reduction in the amount of co-accelerator in the mixture, very good vulcanization behaviour is achieved, specifically high vulcanization rate with sufficiently low level of processing risk.

Another advantage of the inventive rubber mixtures is that no high-volatility alcohol, normally methanol or ethanol, is liberated from the resultant organosilicon compounds of the general formula I. Coupling between filler and polymer is not adversely affected thereby. Coupling of the incorporated organosilicon compounds to the oxidic filler takes place within an economically acceptable period of time.

The involatile silicon substituents that can be cleaved via hydrolysis, e.g. triethanolamine or triisopropanolamine, are hydrolysed at a sufficient rate and at least to some extent eliminated from the fundamental silane structure, the result being sufficient coupling of the organosilicon compounds to the filler during the mixing process. The consequence is a high level of reinforcement in the inventive rubber vulcanizates.

Triethanolamine and triisopropanolamine have boiling points >240° C. at atmospheric pressure and are therefore not volatile organic compounds (VOC).

EXAMPLES

The following raw materials are used for the examples:
Triethanolamine:
The triethanolamine used is from BASF AG and its water content is 0.28 mg/kg.
Bis(triethoxysilylpropyl)polysulphides:
Si 261 from Degussa AG
The bis(triethoxysilylpropyl)polysulphide Si 261 used for the experiments contains, according to NMR analysis, 8.1% by weight of bis(triethoxysilylpropyl)monosulphide, 73.9% by weight of bis(triethoxysilylpropyl)disulphide, 14.7% by weight of bis(triethoxysilylpropyl)trisulphide and 1.8% by weight of bis(triethoxysilylpropyl)tetrasulphide. The average chain length determined for the polysulphide mixture is 2.09 (the S1-S5 average value being taken). The bis(triethoxysilylpropyl)polysulphide used comprises 0.9% by weight of 3-chloropropyl(triethoxysilane). The monomer content is 88% by weight.
Si 262 from Degussa AG
The bis(triethoxysilylpropyl)polysulphide Si 262 used for the experiments contains, according to NMR analysis, 0.3% by weight of bis(triethoxysilylpropyl)monosulphide, 56.8% by weight of bis(triethoxysilyl-propyl)disulphide, 27.7% by weight of bis(triethoxy-silylpropyl)trisulphide and 9.9% by weight of bis(triethoxysilylpropyl)tetrasulphide. The average chain length determined for the polysulphide mixture is 2.62 (the S1-S10 average value being taken). The bis(triethoxysilylpropyl)polysulphide used comprises 0.2% by weight of 3-chloropropyl(triethoxysilane). The monomer content is 95% by weight.
Si 266/2 from Degussa AG
The bis(triethoxysilylpropyl)polysulphide Si 266/2 used for the experiments contains, according to NMR analysis, 6.8% by weight of bis(triethoxysilylpropyl)monosulphide, 91.3% by weight of bis(triethoxysilyl-propyl)disulphide and 0.6% by weight of bis(triethoxy-silylpropyl)trisulphide. The average chain length determined for the polysulphide mixture is 1.93 (the S1-S10 average value being taken). The bis(triethoxy-silylpropyl)polysulphide used comprises 0.9% by weight of 3-chloropropyl(triethoxysilane). The monomer content is 96% by weight.
Si 266 from Degussa AG
The bis(triethoxysilylpropyl)polysulphide Si 266 used for the experiments contains, according to NMR analysis, 2.2% by weight of bis(triethoxysilylpropyl)monosulphide, 80.9% by weight of bis(triethoxysilyl-propyl)disulphide, 13.1% by weight of bis(triethoxy-silylpropyl)trisulphide, 2.0% by weight of bis(triethoxysilylpropyl)tetrasulphide and 1.2% by weight of bis(triethoxysilylpropyl)pentasulphide. The average chain length determined for the polysulphide mixture is 2.2 (the S1-S10 average value being taken). The bis(triethoxysilylpropyl)polysulphide used comprises 0.5% by weight of 3-chloropropyl(triethoxy-silane). The monomer content is 87.6% by weight, determined via $^{29}$Si NMR.
Si 69 from Degussa AG
The bis(triethoxysilylpropyl)polysulphide Si 69 used for the experiments contains, according to $^1$H NMR analysis, 18.2% by weight of bis(triethoxysilylpropyl)disulphide, 26.9% by weight of bis(triethoxy-silylpropyl)trisulphide and 24.2% by weight of bis(triethoxysilylpropyl)tetrasulphide. The average chain length determined for the polysulphide mixture is 3.72 (the S1-S10 average value being taken). The bis(triethoxysilylpropyl)polysulphide used comprises 1.9% by weight of 3-chloropropyl(triethoxysilane). The monomer content is 93% by weight.
Si 69 from Rizhao Lanxing
The bis(triethoxysilylpropyl)polysulphide Si 69 from Rizhao Lanxing used for the experiments contains, according to $^1$H NMR analysis, 16.9% by weight of bis(triethoxysilyl-propyl)disulphide, 23.8% by weight of bis(triethoxysilylpropyl)trisulphide, 24.5% by weight of bis(triethoxysilylpropyl)tetrasulphide and 34.7% by weight of bis (triethoxysilylpropyl)penta-sulphide or longer-chain polysulphide silanes. The average chain length determined for the polysulphide mixture is 3.7 (the S1-S10 average value being taken). The bis(triethoxysilylpropyl)polysulphide used comprises 0.5% by weight of 3-chloropropyl(triethoxy-silane). The monomer content is 87.1% by weight.

Example 1

400 g of bis(triethoxysilylpropyl)polysulphide Si 69 from Degussa AG are mixed in a distillation apparatus with 224.2 g of triethanolamine, 2 g of 2,6-di-tert-butyl-4-methylphenol (Ionol CP) and 0.6 g of titanium tetrabutoxide at room temperature. The oil bath used for heating is heated to 100° C. and ethanol produced is removed by distillation at 200 mbar. After about 150 ml of ethanol have been removed by distillation, the temperature of the oil bath is increased to 160° C. and the pressure is lowered to 100 mbar. When distillation gives no further ethanol, the mixture is heated for a further 120 min at 160° C. and 50 mbar. 2 g of 3-glycidyloxypropyl(triethoxysilane) (Dynasylan GLYEO from Degussa AG) are then added and the mixture is stirred for a further 30 min at 160° C. in vacuo. The black product is poured under argon into a coated mould and solidifies. The product obtained is 403.5 g of a black solid.

According to $^1$H NMR analysis, the product comprises 29.8% by weight of bis(silatranylpropyl)disulphide, 34.1% by weight of bis(silatranylpropyl)trisulphide and 35.2% by weight of bis(silatranylpropyl)tetrasulphide. The average chain length determined for the polysulphide mixture is 3.0 (the S1-S10 average value being taken).

The total chloride content of the material from Example 1 is <0.2% by weight.

Example 2

400 g of bis(triethoxysilylpropyl)polysulphide Si 261 are mixed in a distillation apparatus with 247.7 g of triethanolamine and 1 g of titanium tetrabutoxide at room temperature. The oil bath used for heating is heated to 150° C. and ethanol produced is removed by distillation at from 200 to 600 mbar. The internal temperature rises within a period of 180 min from 135° C. to 148° C. After the distillation process has ended, the brownish product is poured under argon into a coated mould and solidifies. The product obtained is 420.1 g of a dark brown solid.

According to 29 Si NMR analysis, the product comprises 8.7% by weight of bis(silatranylpropyl)monosulphide, 77.2% by weight of bis(silatranylpropyl)disulphide, 12.6% by weight of bis(silatranylpropyl)trisulphide and 1.5% by weight of bis(silatranylpropyl)tetrasulphide. The average chain length determined for the polysulphide mixture is 2.1 (the S1-S10 average value being taken).

Example 3

400 g of bis(triethoxysilylpropyl)polysulphide Si 262 are mixed in a distillation apparatus with 247.7 g of triethanolamine and 0.7 g of titanium tetrabutoxide at room temperature. The oil bath used for heating is heated to 160° C. and ethanol produced is removed by distillation at from 50 to 400 mbar. The internal temperature rises within a period of 90 min to 159° C. After the distillation process has ended, the black product is poured under argon into a coated mould and solidifies. The product obtained is 413.7 g of a brittle black solid.

According to $^{29}$Si NMR analysis, the product comprises 70.2% by weight of bis(silatranylpropyl)disulphide, 22.0% by weight of bis(silatranylpropyl)trisulphide and 3.1% by weight of bis(silatranylpropyl)tetrasulphide. The average chain length determined for the polysulphide mixture is 2.3 (the S1-S10 average value being taken).

Example 4

400.2 g of bis(triethoxysilylpropyl)polysulphide Si 266 having an average —$S_x$— chain length of 2.2 are mixed in a distillation apparatus with 250.7 g of triethanolamine and 1.3 g of titanium tetrabutoxide at room temperature. The oil bath used for heating is heated to 130° C. and ethanol produced is removed by distillation at from 20 to 400 mbar. When no further ethanol is distilled, the product is poured under argon into a coated mould and solidifies. The product obtained is 423 g of a brittle, dark yellow solid.

According to $^1$H NMR analysis, the product comprises 2.5% by weight of bis(silatranylpropyl)monosulphide, 77% by weight of bis(silatranylpropyl)disulphide, 17.5% by weight of bis(silatranylpropyl)trisulphide and 2% by weight of bis(silatranylpropyl)tetrasulphide. The average chain length determined for the polysulphide mixture is 2.2 (the S1-S10 average value being taken).

Example 5

500 g of bis(triethoxysilylpropyl)polysulphide Si 69 from Rizhao Lanxing having an average —$S_x$— chain length of 3.7 are mixed in a distillation apparatus with 280.3 g of triethanolamine and 1 g of titanium tetrabutoxide at room temperature. The oil bath used for heating is heated to 130° C. and ethanol produced is removed by distillation at from 20 to 400 mbar. When the distillation process gives no further ethanol, the mixture is heated for a further 60 min at 130° C. and 20 mbar. The black product is poured under argon into a coated mould and solidifies. The product obtained is 521 g of a black solid.

According to $^1$H NMR analysis, the product comprises 15.7% by weight of bis(silatranylpropyl)disulphide, 29.7% by weight of bis(silatranylpropyl)trisulphide, 32.7% by weight of bis(silatranylpropyl)tetrasulphide and 21.9% by weight of bis(silatranylpropyl)polysulphide having a > —$S_4$— sulphur chain. The average chain length determined for the polysulphide mixture is 3.6 (the S1-S10 average value being taken).

Example 6

400 g of bis(triethoxysilylpropyl)polysulphide Si 266/2 are mixed in a distillation apparatus with 251.2 g of triethanolamine and 1.6 g of titanium tetrabutoxide at room temperature. The oil bath used for heating is heated to 160° C. and ethanol produced is removed by distillation at from 40 to 600 mbar. The internal temperature rises as a function of the pressure applied from 118° C. to 154° C. After 210 min of reaction time at a temperature >120° C. and when the distillation process has ended, the brownish product is poured under argon into a coated mould and solidifies. The product obtained is 422.2 g of a brittle brownish solid.

According to $^1$H NMR analysis, the product comprises 4.6% by weight of bis(silatranylpropyl)monosulphide, 93.8% by weight of bis(silatranylpropyl)disulphide and 1.5% by weight of bis(silatranylpropyl)trisulphide. The average chain length determined for the polysulphide mixture is 1.97 (the S1-S10 average value being taken).

DSC (differential scanning calorimetry) on the material from Example 6 shows a melting point of from 151 to 154° C. (peak of melting curve).

The total chloride content of the material from Example 6 is <0.1% by weight

Example 7

Rubber Mixtures

The mixing specification used for the rubber mixtures is stated in Table 1 below. The unit phr here is parts by weight, based on 100 parts of the crude rubber used. The silanes are added in equimolar amounts, i.e. an equal molar amount is used. The general process for preparation of rubber mixtures and their vulcanizates is described in the book: "Rubber Technology Handbook", W. Hofmann, Hanser Verlag 1994.

TABLE 1

| Substance | Mixture 1 ref. [phr] | Mixture 2 ref. [phr] | Mixture 3 ref. [phr] | Mixture 4 [phr] | Mixture 5 [phr] | Mixture 6 [phr] | Mixture 7 [phr] | Mixture 8 [phr] |
|---|---|---|---|---|---|---|---|---|
| 1st stage | | | | | | | | |
| Buna VSL 5025-1 | 96 | 96 | 96 | 96 | 96 | 96 | 96 | 96 |
| Buna CB 24 | 30 | 30 | 30 | 30 | 30 | 30 | 30 | 30 |
| Ultrasil 7000 GR | 80 | 80 | 80 | 80 | 80 | 80 | 80 | 80 |
| Si 266 | 5.8 | 5.8 | — | — | — | — | — | — |
| Example 4 | — | — | 6 | 6 | 6 | 6 | 6 | 6 |
| ZnO | 3 | 3 | 3 | 3 | 3 | 3 | 3 | 3 |
| Stearic acid | 2 | 2 | 2 | 2 | 2 | 2 | 2 | 2 |
| Naftolen ZD | 10 | 10 | 10 | 10 | 10 | 10 | 10 | 10 |
| Vulkanox 4020 | 1.5 | 1.5 | 1.5 | 1.5 | 1.5 | 1.5 | 1.5 | 1.5 |
| Protektor G 3108 | 1 | 1 | 1 | 1 | 1 | 1 | 1 | 1 |
| 2nd stage | | | | | | | | |
| Stage 1 batch | | | | | | | | |
| 3rd stage | | | | | | | | |
| Stage 2 batch | | | | | | | | |
| Vulkacit D | 2 | 0.1 | 2 | 1 | 0.5 | 0.2 | 0.1 | 0 |
| Vulkacit CZ | 1.5 | 1.5 | 1.5 | 1.5 | 1.5 | 1.5 | 1.5 | 1.5 |
| Perkacit TBzTD | 0.2 | 0.2 | 0.2 | 0.2 | 0.2 | 0.2 | 0.2 | 0.2 |
| Sulphur | 2.1 | 2.1 | 2.1 | 2.1 | 2.1 | 2.1 | 2.1 | 2.1 |

The polymer VSL 5025-1 is a solution-polymerized SBR copolymer from Bayer AG whose styrene content is 25% by weight and whose butadiene content is 75% by weight. The copolymer comprises 37.5 phr of oil and its Mooney viscosity (ML 1+4/100° C.) is 50.

The polymer Buna CB 24 is a cis-1,4-polybutadiene (neodymium type) from Bayer AG, having cis-1,4 content of at least 96% and Mooney viscosity of 44±5.

Ultrasil 7000 GR is a readily dispersible silica from Degussa AG, its BET surface area being 170 m$^2$/g.

The aromatic oil used comprises Naftolen ZD from Chemetall, and Vulkanox 4020 is PPD from Bayer AG and Protektor G3108 is an antiozonant wax from Paramelt B.V. Vulkacit D (DPG) and Vulkacit CZ (CBS) are commercially available products from Bayer AG. Perkacit TBzTD (tetrabenzylthiuram tetrasulphide) is a product from Flexsys N.V.

The rubber mixtures are prepared in an internal mixer in accordance with the mixing specification in Table 2.

TABLE 2

| Stage 1 | |
|---|---|
| Settings | |
| Mixing assembly | Werner & Pfleiderer E-type |
| Rotation rate | 70 min$^{-1}$ |
| Ram pressure | 5.5 bar |
| Capacity | 1.58 L |
| Fill level | 0.56 |
| Chamber temp. | 80° C. |
| Mixing procedure | |
| 0-1 min | Buna VSL 5025-1 + Buna CB 24 |
| 1-2 min | ½ silica, ZnO, stearic acid, Naftolen ZD, coupling agent |
| 2-4 min | ½ silica, Vulkanox, Protektor |
| 4 min | Purge |
| 4-5 min | Mix |
| 5 min | Aerate |
| 5-6 min | Mix and discharge |
| Batch temp. | 150-160° C. |
| Storage | 24 h at room temperature |
| Stage 2 | |
| Settings | |
| Mixing assembly | As in stage 1 except: |
| Rotation rate | 80 min$^{-1}$ |
| Chamber temp. | 80° C. |
| Fill level | 0.54 |
| Mixing procedure | |
| 0-2 min | Break up stage 1 batch |
| 2-5 min | Maintain 155° C. batch temperature via rotation rate variation |
| 5 min | Discharge |
| Batch temp. | 150-160° C. |
| Storage | 4 h at room temperature |
| Stage 3 | |
| Settings | |
| Mixing assembly | As in stage 1 except |
| Rotation rate | 40 min$^{-1}$ |
| Fill level | 0.52 |
| Chamber temp. | 50° C. |
| Mixing procedure | |
| 0-2 min | Stage 2 batch, accelerator, discharge |
| 2 min | and form sheet on laboratory mixing rolls (diameter 200 mm, length 450 mm, chamber temperature 50° C.) Homogenization: Cut the material 5 times towards the left and 5 times towards the right and 6 times with wide nip (6 mm) and 3 times with narrow nip (3 mm) Peel milled sheet away. |
| Batch temp. | <110° C. |

Table 3 collates the methods for rubber testing.

TABLE 3

| Physical testing | Standard/conditions |
|---|---|
| ML 1 + 4, 100° C., 2$^{nd}$ stage, 3$^{rd}$ stage | DIN 53523/3, ISO 667 |
| Prevulcanization behaviour, 130° C. Prevulcanization time t$_5$ | DIN 53523/4, ISO 667 |

TABLE 3-continued

| Physical testing | Standard/conditions |
| --- | --- |
| Prevulcanization time $t_{35}$ Vulcameter testing, 165° C. Dmax – Dmin (dNm) t10% (min) and t90% (min) t80% – t20% (min) | DIN 53529/3, ISO6502 |
| Ring tensile test, 23° C. Tensile strength (MPa) Elongation at break (%) | DIN 53504, ISO 37 |
| Shore A hardness, 23° C. (SH) | DIN 53 505 |
| Compression set | DIN 53 517, ISO 815 |

Table 4 shows the results of vulcanizate testing.

TABLE 4

| | | Mixture No. | | | | | | | |
| --- | --- | --- | --- | --- | --- | --- | --- | --- | --- |
| | | 1 | 2 | 3 | 4 | 5 | 6 | 7 | 8 |
| ML (1 + 4) | [ME] | 66 | 66 | 62 | 63 | 64 | 64 | 65 | 66 |
| t5 | [min] | 34.2 | >60 | 12.2 | 18.9 | 25.1 | 29.8 | 33.2 | 33.5 |
| t35 | [min] | 40.3 | >60 | 16.2 | 23.7 | 30.4 | 35.6 | 39.5 | 40.3 |
| Dmax-Dmin | [dNm] | 14.6 | 14.7 | 16.8 | 16.4 | 16.1 | 16.1 | 15.7 | 15.6 |
| t 10% | [min] | 2.6 | 4.9 | 1.1 | 1.7 | 2.2 | 2.5 | 2.6 | 2.8 |
| t 90% | [min] | 7.1 | 21.2 | 5.1 | 5.0 | 6.1 | 6.9 | 7.3 | 7.6 |
| t 80%-t 20% | [min] | 2.2 | 8.3 | 2.0 | 1.6 | 1.9 | 2.1 | 2.3 | 2.3 |
| Tensile strength | [MPa] | 13.0 | 14.4 | 14.2 | 13.8 | 14.7 | 14 | 15.5 | 14 |
| Elongation at break | [%] | 350 | 410 | 360 | 360 | 390 | 380 | 410 | 390 |
| Shore A hardness | [SH] | 60 | 59 | 63 | 62 | 63 | 62 | 62 | 62 |
| Compression set | [%] | 7.6 | 12.1 | 6.9 | 7.3 | 7.5 | 8.5 | 8.2 | 9 |

The use of accelerator combinations, primary accelerator plus co-accelerator, as in the present example of sulphenamide (CBS) and guanidine (DPG), is widespread in rubber technology. Reasons are firstly the synergistic effects in relation to degree of crosslinking and vulcanization rate (Bayer AG, Handbuch für die Gummiindustrie [Handbook for the rubber industry], $2^{nd}$ edition, 1991, page 384) and secondly the excellent mechanical properties of the rubber mixtures using guanidines as co-accelerator (Werner Hofmann, Vulcanization and Vulcanizing Agents, 1967, page 181).

The ideal vulcanization characteristic of a rubber mixture is a rectangular curve (Bayer AG, Handbuch für die Gummiindustrie, $2^{nd}$ edition, 1991, page 360-361). This means firstly that the incubation time is maximized in order that the rubber mixture can flow properly into the mould provided. This incubation time can be characterized via the t10% time. Secondly, the intention is to minimize the reaction time, in order to ensure that cycle times are short. This reaction time can be characterized via the t80%-t20% time. In summary, the intention is therefore to maximize t10% and minimize t80%-t20%.

FIG. 1 shows the vulcameter curves for mixtures 1, 2, 3 and 7.

When mixtures 1 and 2 are compared it is clear that when a small amount of DPG (mixture 2) is used with the standard silane the vulcameter curve obtained is unsatisfactory. After 30 min, maximum torque has not been achieved, and vulcanization has therefore not been completed. In comparison with this, mixture 1 achieves the necessary plateau after as little as 15 min. The numerical Table 4 shows the unsatisfactory vulcanization characteristic of mixture 2 via high t90% and t80%-t20% values. In comparison with this, with the silane in mixture 7 and a small amount of DPG the vulcanization behaviour seen is equivalent to that of reference mixture 1. The associated data in the numerical table for the t10%, t90% and t80%-t20% values are almost identical and the two vulcameter curves moreover are close to one another. Mixture 8, without any DPG at all, likewise shows almost identical values. It appears that when silanes of the general formula I are used in the inventive rubber mixtures, contrary to the prior art, the amount of co-accelerator can be markedly reduced or indeed omitted while nevertheless ensuring that the vulcanization characteristic is very good.

Example 8

Rubber Mixtures

The rubber mixtures are prepared with the compounds from Examples 2 and 5. As in the previous example, addition is equimolar. Table 5 states the mixing specification. The mixtures are prepared as stated in Table 2 and tested as described in Table 3.

TABLE 5

| Substance | Mixture 9 Ref. [phr] | Mixture 10 Ref. [phr] | Mixture 11 Ref. [phr] | Mixture 12 [phr] | Mixture 13 [phr] | Mixture 14 [phr] | Mixture 15 [phr] | Mixture 16 [phr] |
| --- | --- | --- | --- | --- | --- | --- | --- | --- |
| 1st stage | | | | | | | | |
| Buna VSL 5025-1 | 96 | 96 | 96 | 96 | 96 | 96 | 96 | 96 |
| Buna CB 24 | 30 | 30 | 30 | 30 | 30 | 30 | 30 | 30 |
| Ultrasil 7000 GR | 80 | 80 | 80 | 80 | 80 | 80 | 80 | 80 |
| Si 69 | 6.4 | 6.4 | — | — | — | — | — | — |
| Example 5 | — | — | 6.6 | 6.6 | 6.6 | 6.6 | 6.6 | 6.6 |
| ZnO | 3 | 3 | 3 | 3 | 3 | 3 | 3 | 3 |
| Stearic acid | 2 | 2 | 2 | 2 | 2 | 2 | 2 | 2 |
| Naftolen ZD | 10 | 10 | 10 | 10 | 10 | 10 | 10 | 10 |

TABLE 5-continued

| Substance | Mixture 9 Ref. [phr] | Mixture 10 Ref. [phr] | Mixture 11 Ref. [phr] | Mixture 12 [phr] | Mixture 13 [phr] | Mixture 14 [phr] | Mixture 15 [phr] | Mixture 16 [phr] |
|---|---|---|---|---|---|---|---|---|
| Vulkanox 4020 | 1.5 | 1.5 | 1.5 | 1.5 | 1.5 | 1.5 | 1.5 | 1.5 |
| Protektor G 3108 | 1 | 1 | 1 | 1 | 1 | 1 | 1 | 1 |
| 2nd stage | | | | | | | | |
| Stage 1 batch | | | | | | | | |
| 3rd stage | | | | | | | | |
| Stage 2 batch | | | | | | | | |
| Vulkacit D | 2 | 0.1 | 2 | 1 | 0.5 | 0.2 | 0.1 | 0 |
| Vulkacit CZ | 1.5 | 1.5 | 1.5 | 1.5 | 1.5 | 1.5 | 1.5 | 1.5 |
| Perkacit TBzTD | 0.2 | 0.2 | 0.2 | 0.2 | 0.2 | 0.2 | 0.2 | 0.2 |
| Sulphur | 1.5 | 1.5 | 1.5 | 1.5 | 1.5 | 1.5 | 1.5 | 1.5 |

Figure 2:
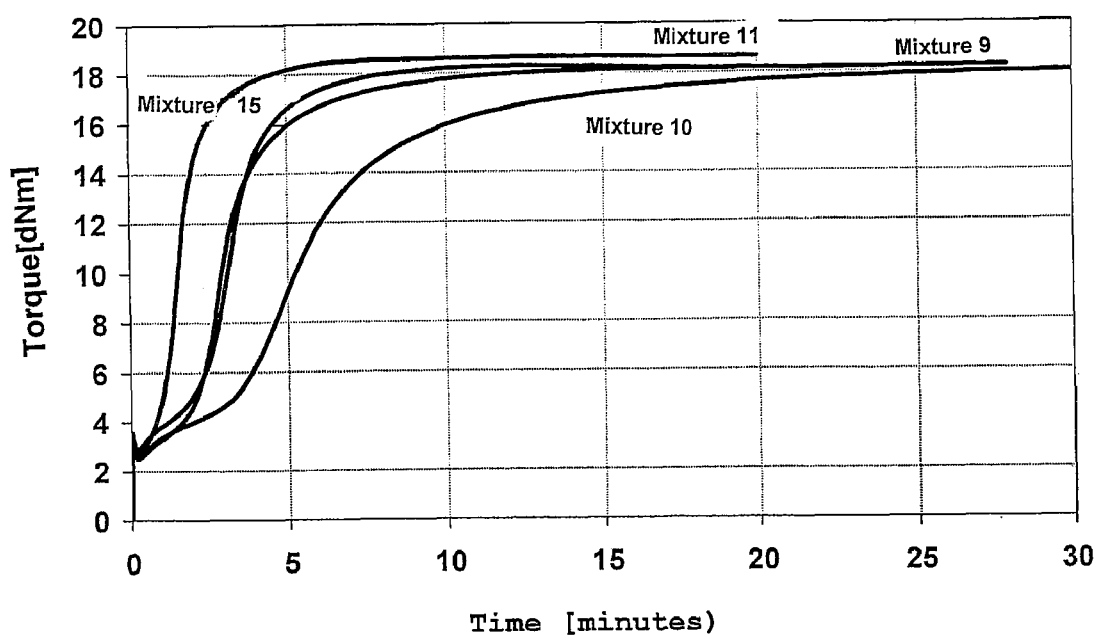
FIG. 2 shows the vulcanizate results of Example 8.

Table 6 and FIG. 2 show the vulcanizate results.

TABLE 6

| | | Mixture No. | | | | | | | |
|---|---|---|---|---|---|---|---|---|---|
| | | 9 | 10 | 11 | 12 | 13 | 14 | 15 | 16 |
| ML (1 + 4) | [MU] | 72 | 73 | 77 | 77 | 79 | 79 | 79 | 85 |
| t5 | [min] | 18.6 | 34.9 | 7.3 | 10.3 | 14.8 | 18.8 | 19.7 | 20.0 |
| t35 | [min] | 24.6 | 44.3 | 10.3 | 14.4 | 19.9 | 24.1 | 25.4 | 26.0 |
| Dmax-Dmin | [dNm] | 15.8 | 15.8 | 16.0 | 15.7 | 15.3 | 15.7 | 15.4 | 15.1 |
| t 10% | [min] | 1.7 | 2.2 | 0.9 | 1.2 | 1.5 | 1.5 | 1.6 | 1.7 |
| t 90% | [min] | 6.0 | 12.6 | 3.1 | 3.8 | 4.7 | 5.0 | 5.2 | 5.4 |
| t 80%-t 20% | [min] | 2.1 | 4.9 | 1.1 | 1.3 | 1.6 | 1.7 | 1.8 | 1.8 |
| Tensile strength | [MPa] | 14.1 | 14.5 | 15.4 | 13.5 | 14.8 | 15 | 13.2 | 14.8 |
| Elongation at break | [%] | 350 | 397 | 365 | 348 | 383 | 377 | 354 | 387 |
| Shore A hardness | [SH] | 60 | 60 | 64 | 63 | 62 | 64 | 63 | 62 |
| Compression set | [%] | 8.2 | 11.2 | 7.8 | 7.7 | 8.1 | 8.9 | 9 | 8.6 |

By analogy with the previous vulcanizate example, equivalent mixtures with compounds are studied here, but with markedly higher average sulphur chain length.

Here again, the graph and the numerical table indicate the same findings. This means that the advantage available from the silatranes is independent of the sulphur chain length of the polysulphide chain.

Example 9

Variation in Discharge Temperature of Mixtures from Kneader

The mixing specification used for the rubber mixtures is stated in Table 7 below. The silanes used comprise Example 6 (mixtures 17-22) and Si 266/2 bis(triethoxysilylpropyl) polysulphide, which was used for its preparation (mixtures 23-26).

TABLE 7

| Substance | Mixtures 17-22 [phr] | Mixtures 23-26 ref. [phr] |
|---|---|---|
| 1st stage | | |
| Buna VSL 5025-1 | 96 | 96 |
| Buna CB 24 | 30 | 30 |
| Ultrasil 7000 GR | 80 | 80 |
| Example 6 | 6 | — |
| Si 266/2 | — | 5.8 |

TABLE 7-continued

| Substance | Mixtures 17-22 [phr] | Mixtures 23-26 ref. [phr] |
|---|---|---|
| ZnO | 3 | 3 |
| Stearic acid | 2 | 2 |
| Naftolen ZD | 10 | 10 |
| Vulkanox 4020 | 1.5 | 1.5 |
| Protektor G 3108 | 1 | 1 |
| 2nd stage | | |
| Stage 1 batch | | |
| 3rd stage | | |
| Stage 2 batch | | |
| Vulkacit D | 0 | 2 |
| Vulkacit CZ | 1.5 | 1.5 |
| Perkacit TBzTD | 0.2 | 0.2 |
| Sulphur | 2.1 | 2.1 |

The mixtures are prepared in accordance with the mixing specification in Table 2. However, the different mixing conditions listed below in Table 8 are used for mixtures 17-22 in order to bring about the differing mixing temperatures. Vulcanizate parameters are studied in accordance with the tests listed in Table 3.

TABLE 8

| Stage 1 | Unit | Mixture 17 | Mixture 18 | Mixture 19 | Mixture 20 | Mixture 21 | Mixture 22 |
|---|---|---|---|---|---|---|---|
| Chamber temperature | [° C.] | 70 | 70 | 80 | 80 | 90 | 90 |
| Rotation rate | [min$^{-1}$] | 60 | 60 | 60 | 70 | 80 | 80 |
| Mixing temperature | [° C.] | 139 | 150 | 161 | 170 | 180 | 189 |

| Stage 2 | Unit | Mixture 15 | Mixture 16 | Mixture 17 | Mixture 18 | Mixture 19 | Mixture 20 |
|---|---|---|---|---|---|---|---|
| Chamber temperature | [° C.] | 80 | 80 | 85 | 85 | 90 | 90 |
| Rotation rate | [min$^{-1}$] | 70 | 70 | 80 | 80 | 90 | 100 |
| Mixing temperature | [° C.] | 139 | 150 | 161 | 170 | 180 | 189 |

Table 9 shows the results.

TABLE 9

| Crude mixture data | Unit | Mixture 17 | Mixture 18 | Mixture 19 | Mixture 20 | Mixture 21 | Mixture 22 |
|---|---|---|---|---|---|---|---|
| ML 1 + 4, 2$^{nd}$ stage | [—] | 77 | 72 | 68 | 69 | 69 | 74 |
| ML 1 + 4, 3$^{rd}$ stage | [—] | 66 | 62 | 60 | 61 | 61 | 62 |
| t5 | [min] | 32.8 | 39.1 | 46.0 | 44.9 | 44.5 | 43.9 |
| t35 | [min] | 37.3 | 45.6 | 51.8 | 50.7 | 50.0 | 49.3 |
| Dmax-Dmin | [dNm] | 18.4 | 16.3 | 14.5 | 14.0 | 12.6 | 11.7 |
| t10% | [min] | 1.9 | 2.7 | 3.4 | 3.5 | 3.8 | 4.0 |

| Vulcanizate data | Unit | Mixture 15 | Mixture 16 | Mixture 17 | Mixture 18 | Mixture 19 | Mixture 20 |
|---|---|---|---|---|---|---|---|
| Tensile strength | [MPa] | 14.3 | 14.7 | 13.8 | 13.1 | 13.4 | 12.5 |
| 100% stress value | [MPa] | 1.8 | 1.7 | 1.6 | 1.6 | 1.6 | 1.6 |
| 300% stress value | [MPa] | 8.6 | 8.6 | 8.5 | 8.7 | 9.3 | 9.5 |
| 300%/100% stress value | [—] | 4.8 | 5.1 | 5.3 | 5.4 | 5.8 | 5.9 |
| Elongation at break | [%] | 410 | 410 | 400 | 380 | 375 | 350 |
| Shore A hardness | [SH] | 65 | 64 | 60 | 59 | 57 | 57 |
| 60° C. ball rebound | [%] | 60.6 | 61.9 | 63.7 | 63.7 | 65.1 | 63.7 |
| DIN abrasion | [mm$^3$] | 94 | 87 | 91 | 87 | 87 | 86 |
| E*, 0° C. | [MPa] | 22.3 | 17.2 | 15.8 | 15.0 | 12.9 | 13.1 |
| tan δ, 60° C. | [—] | 0.126 | 0.120 | 0.118 | 0.118 | 0.114 | 0.118 |

As is discernible from the results in Table 9, the processing of the crude mixtures improves with rising mixing temperature. This is discernible from the improved Mooney scorch of the mixture with high mixing temperature (160° C.-190° C.) in comparison with the mixtures with low mixing temperature (140° C.-150° C.). The prevulcanization behaviour (t10%) also improves continuously with rising mixing temperature.

This is surprising, since Si 266/2 shows behaviour which is precisely the opposite of this (Table 10). The mixtures with the highest mixing temperature have the lowest Mooney scorch and t10% values.

TABLE 10

| Crude mixture data | Unit | Mixture 23 | Mixture 24 | Mixture 25 | Mixture 26 |
|---|---|---|---|---|---|
| Mixing temperature stage 1 | [° C.] | 125 | 144 | 163 | 183 |
| Mixing | | 125 | 147 | 165 | 176 |

TABLE 10-continued

| Crude mixture data | Unit | Mixture 23 | Mixture 24 | Mixture 25 | Mixture 26 |
|---|---|---|---|---|---|
| temperature stage 2 | | | | | |
| t5 | [min] | 39.4 | 46.8 | 37.6 | 22.9 |
| t35 | [min] | 44.3 | 54.9 | 43.8 | 25.5 |
| Dmax-Dmin | [dNm] | 20.7 | 17.7 | 14.8 | 13.8 |
| t 10% | [min] | 2.2 | 3.0 | 2.8 | 2.1 |

It is also discernible from Table 9 that in the case of the mixtures with the organosilicon compounds of the general formula I some of the vulcanizate data improve with rising mixing temperature. Among these are the static moduli, the reinforcement factor and the dynamic modulus E* at 0° C.

Example 10

350 g of Si 266 bis(triethoxysilylpropyl)polysulphide are mixed in a distillation apparatus at room temperature with 280 g of triisopropanolamine (Aldrich) and 2 g of NaOH. The ethanol produced is removed by distillation at 95-105° C. and 40-600 mbar. After 350 min of reaction time and when distillation is complete, the viscous oily product is poured under inert gas into a cooled PE flask. 405 g of a colourless viscous product are isolated.

$^1$H NMR analysis shows that the product comprises a mixture of diastereomers of the general formula

[N(CH$_2$—CH(Me)—O—)$_3$Si(CH$_2$)$_3$]S$_x$[(CH$_2$)$_3$Si(—O—CH(Me)—CH$_2$)$_3$N].

$^{29}$Si NMR analysis shows that the product comprises 92 mol % of [N(CH$_2$—CH(Me)—O—)$_3$Si(CH$_2$)$_3$]S$_2$[(CH$_2$)$_3$Si(—O—CH(Me)—CH$_2$)$_3$N].

Si NMR shows that >98% of all of the Si—OEt bonds have been replaced.

Example 11

Vulcanizate Study on the Compound from Example 10

The mixing specification used for the vulcanizate study is shown in Table 11. The mixing specification for preparation of the rubber mixtures is stated in Table 2. Table 3 lists the vulcanizate tests. The amounts added of the silanes used are equimolar.

TABLE 11

| Substance | Mixture 27 ref. [phr] | Mixture 28 ref. [phr] | Mixture 29 ref. [phr] | Mixture 30 [phr] | Mixture 31 [phr] | Mixture 32 [phr] | Mixture 33 [phr] | Mixture 34 [phr] |
|---|---|---|---|---|---|---|---|---|
| 1$^{st}$ stage | | | | | | | | |
| Buna VSL 5025-1 | 96 | 96 | 96 | 96 | 96 | 96 | 96 | 96 |
| Buna CB 24 | 30 | 30 | 30 | 30 | 30 | 30 | 30 | 30 |
| Ultrasil 7000 GR | 80 | 80 | 80 | 80 | 80 | 80 | 80 | 80 |
| Si 266 | 5.8 | 5.8 | — | — | — | — | — | — |
| Example 10 | — | — | 6.6 | 6.6 | 6.6 | 6.6 | 6.6 | 6.6 |
| ZnO | 3 | 3 | 3 | 3 | 3 | 3 | 3 | 3 |
| Stearic acid | 2 | 2 | 2 | 2 | 2 | 2 | 2 | 2 |
| Naftolen ZD | 10 | 10 | 10 | 10 | 10 | 10 | 10 | 10 |
| Vulkanox 4020 | 1.5 | 1.5 | 1.5 | 1.5 | 1.5 | 1.5 | 1.5 | 1.5 |
| Protektor G 3108 | 1 | 1 | 1 | 1 | 1 | 1 | 1 | 1 |
| 2$^{nd}$ stage | | | | | | | | |
| Stage 1 batch | | | | | | | | |
| 3$^{rd}$ stage | | | | | | | | |
| Stage 2 batch | | | | | | | | |
| Vulkacit D | 2 | 0.1 | 2 | 1 | 0.5 | 0.2 | 0.1 | 0 |
| Vulkacit CZ | 1.5 | 1.5 | 1.5 | 1.5 | 1.5 | 1.5 | 1.5 | 1.5 |
| Perkacit TBzTD | 0.2 | 0.2 | 0.2 | 0.2 | 0.2 | 0.2 | 0.2 | 0.2 |
| Sulphur | 2.1 | 2.1 | 2.1 | 2.1 | 2.1 | 2.1 | 2.1 | 2.1 |

Table 12 collates the results.

TABLE 12

| | | Mixture No. | | | | | | | |
|---|---|---|---|---|---|---|---|---|---|
| | | 27 | 28 | 29 | 30 | 31 | 32 | 33 | 34 |
| ML (1 + 4) | [ME] | 68 | 69 | 60 | 61 | 63 | 65 | 62 | 63 |
| t5 | [min] | 38.9 | >60 | 12.9 | 19.5 | 27.4 | 32.8 | 40.0 | 38.2 |
| t35 | [min] | 47.4 | >60 | 16.5 | 24.2 | 32.4 | 38.8 | 45.8 | 43.3 |
| Dmax-Dmin | [dNm] | 16.2 | 16.8 | 14.5 | 14.7 | 15.3 | 15.4 | 15.4 | 15.5 |
| t 10% | [min] | 2.6 | 3.4 | 1.2 | 1.6 | 2.0 | 2.2 | 2.3 | 2.4 |
| t 90% | [min] | 7.9 | 18.2 | 3.7 | 4.4 | 5.3 | 6.5 | 7.2 | 7.1 |
| t 80%-t 20% | [min] | 2.6 | 7.9 | 1.3 | 1.4 | 1.6 | 2.0 | 2.3 | 2.2 |
| Tensile strength | [MPa] | 12.1 | 13.4 | 14.5 | 13.9 | 13.8 | 15.1 | 14.2 | 14.7 |
| Elongation at break | [%] | 340 | 395 | 445 | 440 | 435 | 460 | 475 | 465 |
| Shore A hardness | [SH] | 61 | 63 | 60 | 62 | 61 | 61 | 61 | 62 |
| Compression set | [%] | 9.3 | 14.8 | 9.7 | 10.4 | 11.2 | 12.2 | 12.7 | 12.4 |

When the results in Table 12 are considered, the advantages for the inventive rubber mixtures here are again the same as those in Example 7. Here again, although the amount of co-accelerator is small or indeed zero a very good vulcanization characteristic is achieved. As described previously, this is discernible in the high t 10% values combined with low t80%-t20% values.

Example 12

Rubber mixtures with Additional Processing Aid

In another example, 4 phr of an ethoxylated alcohol (Lutensol TO 5 from BASF AG) are fed into the inventive rubber mixtures as processing aid. Table 13 states the mixing specifications. The rubber mixtures are prepared in accordance with the mixing specification in Table 2. Lutensol T 05 processing aid is added here simultaneously with the silane. The mixtures are studied in accordance with the tests stated in Table 3. Table 14 collates the results.

TABLE 13

| Substance | Mixture 35 ref. [phr] | Mixture 36 ref. [phr] | Mixture 37 ref. [phr] | Mixture 38 [phr] |
|---|---|---|---|---|
| 1st stage | | | | |
| Buna VSL 5025-1 | 96 | 96 | 96 | 96 |
| Buna CB 24 | 30 | 30 | 30 | 30 |
| Ultrasil 7000 GR | 80 | 80 | 80 | 80 |
| Si 266 | 5.8 | 5.8 | — | — |
| Example 10 | — | — | 6.6 | 6.6 |
| Lutensol T 05 | 4 | 4 | 4 | 4 |
| ZnO | 3 | 3 | 3 | 3 |
| Stearic acid | 2 | 2 | 2 | 2 |
| Naftolen ZD | 10 | 10 | 10 | 10 |
| Vulkanox 4020 | 1.5 | 1.5 | 1.5 | 1.5 |
| Protektor G 3108 | 1 | 1 | 1 | 1 |
| 2nd stage | | | | |
| Stage 1 batch | | | | |
| 3rd stage | | | | |
| Stage 2 batch | | | | |
| Vulkacit D | 2 | 0.1 | 2 | 0.1 |
| Vulkacit CZ | 1.5 | 1.5 | 1.5 | 1.5 |
| Perkacit TBzTD | 0.2 | 0.2 | 0.2 | 0.2 |
| Sulphur | 2.1 | 2.1 | 2.1 | 2.1 |

TABLE 14

| | | Mixture No. | | | |
|---|---|---|---|---|---|
| | | 35 | 36 | 37 | 38 |
| ML (1 + 4) | [MU] | 59 | 59 | 55 | 58 |
| t5 | [min] | 32.7 | >60 | 11.5 | 33.2 |
| t35 | [min] | 38.9 | >60 | 14.6 | 39.0 |
| Dmax-Dmin | [dNm] | 15.1 | 15.3 | 13.8 | 15.1 |
| t 10% | [min] | 2.5 | 4.7 | 1.1 | 2.0 |
| t 90% | [min] | 7.3 | 15.4 | 3.5 | 6.5 |
| t 80%-t 20% | [min] | 2.3 | 5.2 | 1.2 | 2.0 |
| Tensile strength | [MPa] | 11.8 | 12.7 | 13.1 | 14.4 |
| Elongation at break | [%] | 350 | 395 | 475 | 520 |
| Shore A hardness | [SH] | 59 | 60 | 58 | 60 |
| Compression set | [%] | 9.3 | 11.4 | 10.9 | 12.8 |

If the following comparisons are made between mixtures: 27 with 35, 28 with 36, 29 with 37 and 33 with 38, it is discernible that the processing aid significantly lowers Mooney viscosity and thus improves the processing of the crude mixture. The advantages of inventive mixture 38 are retained.

Example 13

512 g of Si 266 bis(triethoxysilylpropyl)polysulphide are mixed in an apparatus with flask and reflux condenser under inert gas at room temperature with 319.2 g of triethanolamine (BASF AG), 700 g of ethanol and 4 g of NaOH. The mixture is heated to 78° C. for 360 min. A further 700 g of ethanol are then added at 50° C., and the mixture is cooled to room temperature and stirred for 16 h.

The colourless product precipitated is removed by filtration, washed with cold ethanol and dried at 60-100° C. and 5-10 mbar. 502 g of product are isolated (M=501.6 g/mol; 94% of theory).

Si NMR shows that >98% of all of the Si—OEt bonds have been replaced. $^1$H NMR analysis shows that the product comprises >91 mol % of compound $[N(CH_2—CH_2—O—)_3Si(CH_2)_3]S_2[(CH_2)_3Si(—O—CH_2—CH_2)_3N]$. The melting range of the product isolated is 142-148° C.

Example 14

256 g of Si 266 bis(triethoxysilylpropyl)polysulphide are mixed in an apparatus with flask and reflux condenser under inert gas at room temperature with 159.5 g of triethanolamine (BASF AG), 700 g of ethanol and 3 g of NaOH. The mixture is stirred for 360 min.

The colourless product precipitated is removed by filtration, washed with 300 g of cold ethanol and dried at 60-100° C. and 5-10 mbar. 215 g of product are isolated (80.2% of theory). Si NMR shows that >97% of all of the Si—OEt bonds have been replaced. $^{29}$Si NMR analysis shows that the product comprises >90 mol % of compound $[N(CH_2—CH_2—O—)_3Si(CH_2)_3]S_2[(CH_2)_3Si(—O—CH_2—CH_2)_3N]$.

Further product (51 g) is obtained from the mother liquor and the wash ethanol via drying.

Example 15

256 g of Si 266 bis(triethoxysilylpropyl)polysulphide are mixed in an apparatus with flask and reflux condenser under inert gas at room temperature with 159.5 g of triethanolamine (BASF AG), 700 g of ethanol and 3 g of finely divided NaOH. The mixture is stirred at 35° C. for 240 min. The mixture is then stirred for 60 min at 0-5° C.

The precipitated, colourless product is removed by filtration and dried at 70-105° C. and 5-10 mbar. 229 g of product are isolated (86% of theory). Si NMR shows that >97% of all of the Si—OEt bonds have been replaced. $^{29}$Si NMR analysis shows that the product comprises >89 mol % of compound $[N(CH_2—CH_2—O—)_3Si(CH_2)_3]S_2[(CH_2)_3Si(—O—CH_2—CH_2)_3N]$.

Further product (33 g) is obtained from the mother liquor via drying.

Example 16

256 g of Si 266 bis(triethoxysilylpropyl)polysulphide are mixed in an apparatus with flask and reflux condenser under inert gas at room temperature with 159.5 g of triethanolamine (BASF AG), 700 g of ethanol and 6 g of powdered NaOH. The mixture is stirred at 35° C. for 120 min.

The colourless product precipitated is removed by filtration at room temperature, washed with ethanol and dried at 65-100° C. and 5-10 mbar. 204 g of product are isolated (77% of theory). Si NMR shows that >98% of all of the Si—OEt bonds have been replaced. The melting range of the product isolated is 142-147° C. $^1$H NMR analysis shows that the product comprises >91 mol % of compound [N(CH$_2$—CH$_2$—O—)$_3$Si(CH$_2$)$_3$]S$_2$—[(CH$_2$)$_3$Si(—O—CH$_2$—CH$_2$)$_3$N].

Further product (64 g) is obtained from the mother liquor and the wash ethanol via drying.

The invention claimed is:

1. A rubber mixture, comprising
   (a) at least one rubber,
   (b) a filler,
   (c) an organosilicon compound of general formula I,

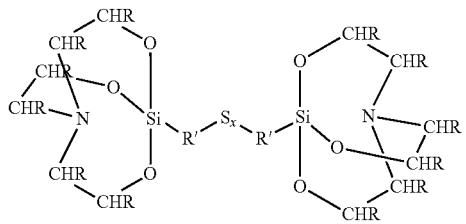

where R is identical or different and is H, a cyclic, straight-chain or branched $C_1$-$C_{12}$-alkyl group, a carboxy group (—COOH), a substituted or unsubstituted aryl group or a substituted or unsubstituted aralkyl group, R' is identical or different and is a branched or unbranched, saturated or unsaturated, aliphatic, aromatic or mixed aliphatic/aromatic divalent $C_1$-$C_{30}$ hydrocarbon group, x is an average chain length of from 1 to 10, (d) from 0.3 to 5% by weight of rubber accelerator, based on the rubber used, selected from the group of the thiazoles, sulphenamides, thiurams, thioureas, thiocarbonates and dithiocarbamates and (e) an amount from 0.1 to 1.5% by weight, based on the rubber used, of co-accelerator, selected from the group of the guanidines and aldehydamines.

2. The rubber mixture according to claim 1, further comprising a rubber auxiliary.

3. The rubber mixture according to claim 2, wherein the rubber auxiliary is polyethylene glycol, polypropylene glycol, polybutylene glycol with molar masses from 50 to 50 000 g/mol, hydrocarbon-terminated polyethylene glycol, Alk-O—(CH$_2$—CH$_2$—O)$_{yI}$—H, Alk-O(CH$_2$—CH$_2$—O)$_{yI}$- Alk, hydrocarbon-terminated polypropylene glycol Alk-O—(CH$_2$—CH(CH$_3$)—O)$_{yI}$—H, Alk-O—(CH$_2$—CH(CH$_3$)—O)$_{yI}$-Alk, hydrocarbon-terminated polybutylene glycol Alk-O—(CH$_2$—CH$_2$—CH$_2$—CH$_2$—O)$_{yI}$—H, Alk-O—(CH$_2$—CH(CH$_3$)—CH$_2$—O)$_{yI}$—H, Alk-O—(CH$_2$—CH$_2$—CH$_2$—CH$_2$—O)$_{yI}$-Alk, or Alk-O—(CH$_2$—CH(CH$_3$)—CH$_2$—O)$_{yI}$-Alk, where the average of yI is from 2 to 25 and Alk is a branched or unbranched, unsubstituted or substituted, saturated or unsaturated hydrocarbon having from 1 to 35 carbon atoms, or is neopentyl glycol HO—CH$_2$—C(Me)$_2$—CH$_2$—OH, pentaerythritol C(CH$_2$—OH)$_4$ or trimethylolpropane CH$_3$—CH$_2$—C(CH$_2$—OH)$_3$ etherified with polyethylene glycol, etherified with polypropylene glycol, etherified with polybutylene glycol, or etherified with a mixture thereof, where the number of repeat units of ethylene glycol, propylene glycol or/and butylene glycol in the etherified polyalcohols is from 2 to 100.

4. A process for preparation of the rubber mixture according to claim 1, comprising mixing together:
   (a) at least one rubber,
   (b) a filler,
   (c) an organosilicon compound of general formula I,
   (d) from 0.3 to 5% by weight of rubber accelerator, based on the rubber used, selected from the group consisting of the thiazoles, sulphenamides, thiurams, thioureas, thiocarbonates and dithiocarbamates and
   (e) an amount from 0.1 to 1.5% by weight, based on the rubber used, of co-accelerator, selected from the group consisting of the guanidines and aldehydamines are mixed.

5. The process for preparation of the rubber mixture according to claim 4, wherein mixing takes place at temperatures of from 90 to 230° C.

6. A moulding made from the rubber mixture according to claim 1.

7. An article of manufacture selected from the group consisting of tires, tire treads, cable sheathing, hoses, drive belts, conveyor belts, roll coverings, shoe soles, sealing rings and damping elements made from the rubber mixture according to claim 1.

8. Process for preparation of the organosilicon compounds of the formula

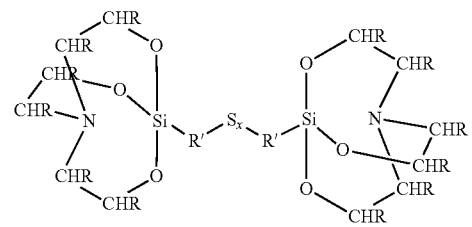

I— as follows where R is identical or different and is H, a cyclic, straight-chain or branched $C_1$-$C_{12}$-alkyl group, a carboxy group (—COOH), a substituted or unsubstituted aryl group or a substituted or unsubstituted aralkyl group, R' is identical or different and is a branched or unbranched, saturated or unsaturated, aliphatic, aromatic or mixed aliphatic/aromatic divalent $C_1$-$C_{30}$ hydrocarbon group, x is an average chain length of from 1 to 10, comprising:
reacting an organosilicon compounds of the formula III:

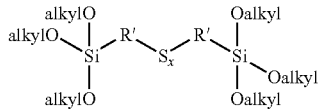

in which R' is as defined above and alkyl is identical or different and said alkyl is a monovalent $C_1$-$C_8$ hydrocarbon radical
in a reaction mixture with a compound of the formula IV

   IV in which R is as defined above, with elimination of alkyl-OH, and
removing alkyl-OH from the reaction mixture,
and using a titanium alkoxide as catalyst.

9. Process according to claim 8, wherein, for organosilicon compounds of the general formula I, where R is H, R' is ($-CH_2-CH_2-CH_2-$), x is from 1.5 to 2.8, an Alkyl-OH is a solvent.

10. Process according to claim 1, wherein the amount of co-accelerator is from 0.1 to 1% by weight, based on the rubber used.

11. Process according to claim 4, wherein the amount of co-accelerator is from 0.1 to 1% by weight, based on the rubber used.

* * * * *